US012773503B2

(12) United States Patent
Kemp et al.

(10) Patent No.: US 12,773,503 B2
(45) Date of Patent: Oct. 27, 2026

(54) AUTO-INJECTOR

(71) Applicant: Sanofi-Aventis Deutschland GMBH, Frankfurt am Main (DE)

(72) Inventors: Thomas Mark Kemp, Ashwell (GB); Timothy Donald Barrow-Williams, St. Albans Herts (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 19/022,522

(22) Filed: Jan. 15, 2025

(65) Prior Publication Data

US 2025/0152843 A1 May 15, 2025

Related U.S. Application Data

(63) Continuation of application No. 17/227,944, filed on Apr. 12, 2021, which is a continuation of application (Continued)

(30) Foreign Application Priority Data

Dec. 21, 2010 (EP) .................................... 10196073

(51) Int. Cl.
*A61M 5/20* (2006.01)
*A61M 5/315* (2006.01)
*A61M 5/32* (2006.01)

(52) U.S. Cl.
CPC ........ *A61M 5/3204* (2013.01); *A61M 5/2033* (2013.01); *A61M 5/326* (2013.01); (Continued)

(58) Field of Classification Search
CPC .. A61M 5/3204; A61M 5/2033; A61M 5/326; A61M 2005/206; A61M 2005/208; (Continued)

(56) References Cited

U.S. PATENT DOCUMENTS 2,605,766 A 8/1952 Uytenbogaart
5,984,899 A * 11/1999 D'Alessio ........... A61M 5/3271 604/198

(Continued)

FOREIGN PATENT DOCUMENTS

GB 2424837 A 10/2006
JP 2008-534204 A 8/2008

(Continued)

OTHER PUBLICATIONS

International Preliminary Report on Patentability in International Application No. PCT/EP2011/073508, issued Jun. 25, 2013, 9 pages.

(Continued)

*Primary Examiner* — Kevin C Sirmons
*Assistant Examiner* — William R Frehe
(74) *Attorney, Agent, or Firm* — Fish & Richardson P.C.

(57) ABSTRACT

An auto-injector comprising an elongate housing containing a syringe. The housing having an orifice intended to be applied against an injection site. The syringe is slidably arranged with respect to the housing. A spring pushing the needle from a covered position into an advanced position, operating the syringe and covering the needle. An activator arranged to lock the spring prior to manual operation and capable of, upon manual operation, releasing the spring means for injection. A first gear arrangement and a second gear arrangement arranged for converting torque from a first end and a second end of the torsion spring into a translative force. The first end ground able in the housing while the second end acts on a plunger through the second gear arrangement for advancing the needle and supplying the dose.

15 Claims, 27 Drawing Sheets

Related U.S. Application Data

No. 15/782,602, filed on Oct. 12, 2017, now Pat. No. 10,973,989, which is a continuation of application No. 13/996,321, filed as application No. PCT/EP2011/073508 on Dec. 21, 2011, now Pat. No. 9,789,261.

(60) Provisional application No. 61/432,241, filed on Jan. 13, 2011.

(52) U.S. Cl.
CPC . *A61M 2005/206* (2013.01); *A61M 2005/208* (2013.01); *A61M 5/31583* (2013.01)

(58) Field of Classification Search
CPC .............. A61M 5/31583; A61M 5/322; A61M 5/3234; A61M 2005/2086
USPC ......................................... 604/192, 193, 198
See application file for complete search history.

(56) References Cited

U.S. PATENT DOCUMENTS

| | | | |
|---|---|---|---|
| 7,427,275 B2 | 9/2008 | DeRuntz et al. | |
| 7,597,685 B2 | 10/2009 | Olson | |
| 7,918,824 B2 | 4/2011 | Bishop et al. | |
| 8,409,138 B2 | 4/2013 | James et al. | |
| 8,734,394 B2 | 5/2014 | Admas et al. | |
| 8,808,250 B2 | 8/2014 | Ekman et al. | |
| 9,044,553 B2 | 6/2015 | James et al. | |
| 9,216,256 B2 | 12/2015 | Olson et al. | |
| 9,233,213 B2 | 1/2016 | Olson et al. | |
| 9,402,957 B2 | 8/2016 | Adams et al. | |
| 9,408,976 B2 | 8/2016 | Olson et al. | |
| 9,789,261 B2 | 10/2017 | Kemp et al. | |
| 9,872,961 B2 | 1/2018 | Fourt et al. | |
| 10,118,001 B2 | 11/2018 | Fourt et al. | |
| 10,314,981 B2 | 6/2019 | Sampson et al. | |
| 10,350,362 B2 | 7/2019 | Dennis, Jr. et al. | |
| 10,363,377 B2 | 7/2019 | Atterbury et al. | |
| 10,420,898 B2 | 9/2019 | Daniel | |
| 10,569,019 B2 | 2/2020 | Hirschel et al. | |
| 10,799,647 B2 | 10/2020 | Hosteettler et al. | |
| 11,298,462 B2 | 4/2022 | Atterburg et al. | |
| 11,383,044 B2 | 7/2022 | Tschirren et al. | |
| 11,452,821 B2 | 9/2022 | Lafever et al. | |
| 2001/0005781 A1* | 6/2001 | Bergens .............. | A61M 5/2033 604/156 |
| 2002/0095120 A1* | 7/2002 | Larsen ................ | A61M 5/2033 604/187 |
| 2004/0039336 A1 | 2/2004 | Amark et al. | |
| 2004/0054327 A1* | 3/2004 | Gillespie, III ...... | A61M 5/2066 604/181 |
| 2005/0101919 A1* | 5/2005 | Brunnberg ............ | A61M 5/326 604/197 |
| 2006/0149190 A1 | 7/2006 | Kohlbrenner et al. | |
| 2006/0211982 A1* | 9/2006 | Prestrelski ........ | A61M 5/31531 604/60 |
| 2006/0287630 A1 | 12/2006 | Hommann | |
| 2007/0112310 A1 | 5/2007 | Lavi et al. | |
| 2008/0051713 A1 | 2/2008 | Kohlbrenner et al. | |
| 2008/0142007 A1 | 6/2008 | Fenlon | |
| 2008/0215001 A1* | 9/2008 | Cowe .................... | A61M 5/326 604/110 |
| 2008/0269691 A1 | 10/2008 | Cowe | |
| 2008/0269692 A1 | 10/2008 | James et al. | |
| 2008/0312602 A1 | 12/2008 | Barrow-Williams et al. | |
| 2009/0005737 A1 | 1/2009 | Chun | |
| 2010/0280460 A1* | 11/2010 | Markussen ........... | A61M 5/322 604/195 |
| 2011/0208119 A1 | 8/2011 | Asmusssen et al. | |
| 2018/0064875 A1 | 3/2018 | Holmqvist | |
| 2019/0374717 A1 | 12/2019 | Swanson et al. | |
| 2021/0228813 A1 | 7/2021 | Kemp et al. | |
| 2025/0152840 A1 | 5/2025 | Kemp et al. | |
| 2025/0152841 A1 | 5/2025 | Kemp et al. | |
| 2025/0152842 A1 | 5/2025 | Kemp et al. | |
| 2025/0152844 A1 | 5/2025 | Kemp et al. | |
| 2025/0152845 A1 | 5/2025 | Kemp et al. | |

FOREIGN PATENT DOCUMENTS

| | | |
|---|---|---|
| JP | 2010-532243 A | 10/2010 |
| JP | 2011-510782 A | 4/2011 |
| JP | 2012-502707 A | 2/2012 |
| WO | WO 1996/032974 A1 | 10/1996 |
| WO | WO 2002/017996 A1 | 3/2002 |
| WO | WO 2002/047746 A1 | 6/2002 |
| WO | WO 2006/106292 A1 | 10/2006 |
| WO | WO 2009/007305 A1 | 1/2009 |
| WO | WO 2009/062508 A1 | 5/2009 |
| WO | WO 2009/098502 A2 | 8/2009 |
| WO | WO 2010/034380 A1 | 4/2010 |
| WO | WO 2010/136077 A1 | 12/2010 |
| WO | WO 2011/048422 A2 | 4/2011 |
| WO | WO 2011/109205 A2 | 9/2011 |
| WO | WO 2019/074788 A1 | 4/2019 |
| WO | WO 2020/190529 A1 | 9/2020 |

OTHER PUBLICATIONS

International Search Report and Written Opinion in International Application No. PCT/EP2011/073508, mailed May 7, 2012, 13 pages.

* cited by examiner

AUTO-INJECTOR

CROSS REFERENCE TO RELATED APPLICATIONS

The present application is a continuation of U.S. patent application Ser. No. 17/227,944, filed on Apr. 12, 2021, which is a continuation of U.S. patent application Ser. No. 15/782,602, filed on Oct. 12, 2017, now U.S. Pat. No. 10,973,989, which is a continuation of U.S. patent application Ser. No. 13/996,321, filed on Jun. 20, 2013, now U.S. Pat. No. 9,789,261, which is a U.S. National Phase Application pursuant to 35 U.S.C. § 371 of International Application No. PCT/EP2011/073508, filed on Dec. 21, 2011, which claims priority to European Patent Application No. 10196073.0, filed on Dec. 21, 2010 and U.S. Provisional Patent Application No. 61/432,241, filed on Jan. 13, 2011. The entire disclosure contents of these applications are herewith incorporated by reference into the present application.

FIELD OF INVENTION

The invention relates to an auto-injector for administering a dose of a liquid medicament and to a method for operating the auto-injector.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

In the context of this specification the term proximal refers to the direction pointing towards the patient during an injection while the term distal refers to the opposite direction pointing away from the patient.

An auto-injector for administering a dose of a liquid medicament according to the invention comprises:

- an elongate housing arranged to contain a syringe with a hollow needle and a stopper for sealing the syringe and displacing the medicament, the elongate housing having a distal end and a proximal end with an orifice intended to be applied against an injection site, wherein the syringe is slidably arranged with respect to the housing,
- spring means capable of, upon activation, pushing the needle from a covered position inside the housing into an advanced position through the orifice and past the proximal end, operating the syringe to supply the dose of medicament, and covering the needle on removal of the auto-injector from the injection site,
- activating means arranged to lock the spring means in a pressurized state prior to manual operation and capable of, upon manual operation, releasing the spring means for injection.

According to one aspect of the invention the spring means is a single torsion spring.

In one embodiment a first gear arrangement and a second gear arrangement are arranged for respectively converting torque from a first end and a second end of the torsion spring into a translative force. The first end is arranged to be groundable in the housing while the second end is configured to act on a plunger through the second gear arrangement for advancing the needle and supplying the dose. The activating means is arranged to block or release the second gear arrangement. When the second gear arrangement is blocked by the activating means the torque from the second end of the torsion spring is also statically resolved in the housing. The first end is releasable from the ground in the housing for causing a translation through the first gear arrangement resulting in the needle getting covered.

This translation may be a needle retraction or preferably the advancement of a needle shroud over the needle.

The single torsion spring is used for both, inserting the needle and fully emptying the syringe. A major advantage of the torsion spring with gear arrangements is that force is exerted on the stopper and syringe in a smooth manner, whereas a conventional compression spring exhibits a rather abrupt force deployment which may spoil a glass syringe or other parts of the auto-injector.

The needle shroud may be arranged in the housing surrounding the syringe and translatable in longitudinal direction, wherein the needle shroud is coupled to the first gear arrangement in a manner to be translated in proximal direction over the advanced needle on release of the first end from the ground in the housing.

The torque required to advance the needle shroud may be configured to be less than the torque required to advance the plunger and the stopper. This allows for triggering the shroud advancement at any point during injection without having to ground the second end of the torsion spring in the housing while injection is immediately stopped.

The first gear arrangement and the second gear arrangement may respectively comprise a first gear member coupled to the respective end of the torsion spring, wherein the first gear member is engaged through a screw thread to a respective second gear member arranged to translate on rotation of the first gear member.

The needle shroud may be arranged to be in an initial position protruding from the proximal end of the housing in an initial state interlocked to the activating means for preventing manual operation. The needle shroud may be arranged to be translated in distal direction into the housing into a distal position against the load of a shroud spring when pushed against the injection site. The needle shroud is rotationally fixed to the housing and to the second gear member of the first gear arrangement. In the distal position the needle shroud is arranged to rotationally fix the first gear member to the second gear member of the first gear arrangement and to allow operation of the activating means. The needle shroud is thus used as a skin interlock means requiring a sequence of operation in order to increase needle safety. Furthermore, the needle shroud serves for blocking the first gear arrangement as long as it is maintained pressed against the injection site. When removed from the skin, the needle shroud returns into the initial position under load of the shroud spring thereby releasing the first gear arrangement for advancing the needle shroud further.

The activating means may be arranged to be in a splined engagement with the first gear member of the first gear arrangement in the initial state so as to rotationally fix it to the housing, wherein the activating means is arranged to remove this splined engagement on manual operation. This ensures that the first end of the torsion spring is grounded in the housing prior to injection. The activating means cannot be operated before the needle shroud has been depressed. On depression of the needle shroud the already grounded first end of the torsion spring becomes further grounded in the housing through the first gear arrangement. Operating the activating means removes only one of these grounds. This ensures that the needle shroud is only advanced over the needle when the needle shroud is allowed to return to the initial position on removal from the injection site after an injection has been triggered.

A clip arrangement may be provided comprising at least one resilient chassis clip attached to the housing. The chassis clip may be engageable proximally behind a shoulder in the plunger in a manner to prevent translation of the plunger in proximal direction. The shoulder may be arranged to flex the chassis clip outwards due to ramped engagement under force in proximal direction applied to the plunger from the second end of the torsion spring through the second gear arrangement. The activation means may comprise an end trigger button arranged at the distal end translatable between a distal position and a proximal position. At least one trigger beam may be arranged on the trigger button in a manner to outwardly support the chassis clip to prevent it from being outwardly deflected when the end trigger button is in the distal position. The trigger beam is arranged to be repositioned on translation of the end trigger button into the proximal position, i.e. depression in a manner to allow outward deflection of the chassis clip thus releasing the plunger for needle insertion and injection. The end trigger button may protrude from the distal end in a manner to be accessible for operation.

At least one flexible first beam element may be arranged on the housing, the flexible first beam element arranged to obstruct the path of the end trigger button so as to prevent its depression. A second beam element is arranged on the needle shroud in a manner to deflect the flexible first beam element out of the path of the end trigger button on depression of the needle shroud. This embodiment requires the user to first depress the needle shroud before the end trigger button can be translated.

In another embodiment a rib may be arranged in the housing in a manner to obstruct the path of a resilient part of the end trigger button so as to prevent depression of the end trigger button. A lateral trigger button may be laterally arranged on the housing arranged to inwardly deflect the resilient part of the end trigger button in a manner to bypass the rib thus allowing depression of the end trigger button. The needle shroud may be arranged to inwardly support the resilient part of the end trigger button when in the initial position so as to prevent deflection. The inward support of the resilient part of the end trigger button is arranged to be removed on translation of the needle shroud into the distal position. The end trigger button is biased in proximal direction against the housing by a trigger spring. In this embodiment the end trigger button may be hidden inside the distal end so only the lateral trigger button is operated by the user.

In yet another embodiment a wrap over sleeve trigger may be arranged over the distal end. The sleeve trigger is translatable in longitudinal direction between a distal position and a proximal position and has at least one locking feature engageable with a respective mating part on the needle shroud in the initial position so as to prevent depression of the sleeve trigger from the distal position into the proximal position. The mating part is arranged to be inwardly withdrawn by a cam feature on translation of the needle shroud into the distal position so as to allow the sleeve trigger to be depressed. The end trigger button exhibits at least one latch feature arranged to abut against a respective stop in the housing so as to prevent depression of the end trigger button. At least one latch actuation boss on the sleeve trigger is arranged to inwardly deflect the latch feature disengaging it from the stop. The end trigger button is biased in proximal direction against the housing by a trigger spring. A wrap over sleeve trigger may ease operation for users with reduced dexterity.

The trigger spring and the shroud spring are specified to balance each other's load. I.e. the relative strength of the shroud spring and the trigger spring are arranged such that when the auto-injector is pressed against the injection site the shroud will always move first thereby giving a two step feel to the operation.

The screw thread of the first gear arrangement may end with a pitch of zero on its proximal end allowing remaining torque in the torsion spring to be released when the second gear member reaches the zero pitch.

According to another aspect of the invention a method for operating the auto-injector comprises the steps of:

grounding the first end of the torsion spring in the housing and blocking the second gear arrangement in an initial state prior to manual operation of the activating means, releasing the second gear arrangement on manual operation of the activating means so as to translate the plunger in proximal direction for advancing the needle and supplying a dose of medicament from the syringe under torque from the second end of the torsion spring, releasing the first end from the ground in the housing for causing a translation through the first gear arrangement under torque from the first end resulting in the needle getting covered.

The first gear arrangement may translate the needle shroud in proximal direction over the advanced needle on release of the first end from the ground in the housing.

The needle shroud may be held in an initial position protruding from the proximal end of the housing in the initial state, wherein the needle shroud is interlocked to the activating means for preventing manual operation in the initial state, wherein the needle shroud is translated in distal direction into the housing into a distal position against the load of a shroud spring when pushed against the injection site. The needle shroud is rotationally fixed to the housing and to the second gear member of the first gear arrangement. In the distal position the needle shroud rotationally fixes a first gear member to the second gear member of the first gear arrangement and releases the interlock so as to allow operation of the activating means.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
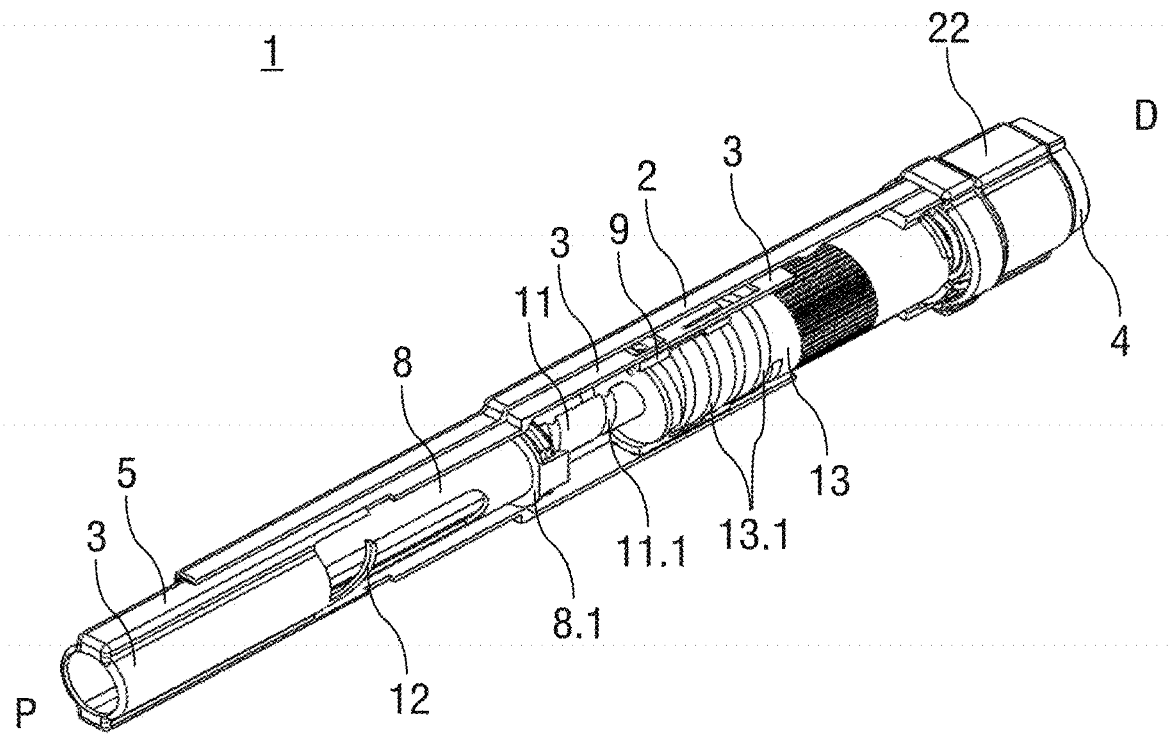
FIG. 1 is an isometric partial section of an auto-injector.

FIG. 1 shows an isometric partial section of an auto-injector 1 with an elongate housing 2 and a needle shroud 3 for protecting a needle (not shown). A trigger button 4 (e.g., an activating member) arranged at a distal end D of the auto-injector 1 may be depressed in a proximal direction P in order to trigger an automatic injection. The trigger button 4 is interlocked with the needle shroud 3 so it cannot be pressed until the needle shroud 3 is pushed into the housing 2 by placing it on an injection site, e.g. a patient's skin and applying pressure. The needle shroud 3 has longitudinal splines 5 engaged in corresponding grooves in the housing 2 for preventing relative rotation of the needle shroud 3 with respect to the housing 2

Figure 2A:
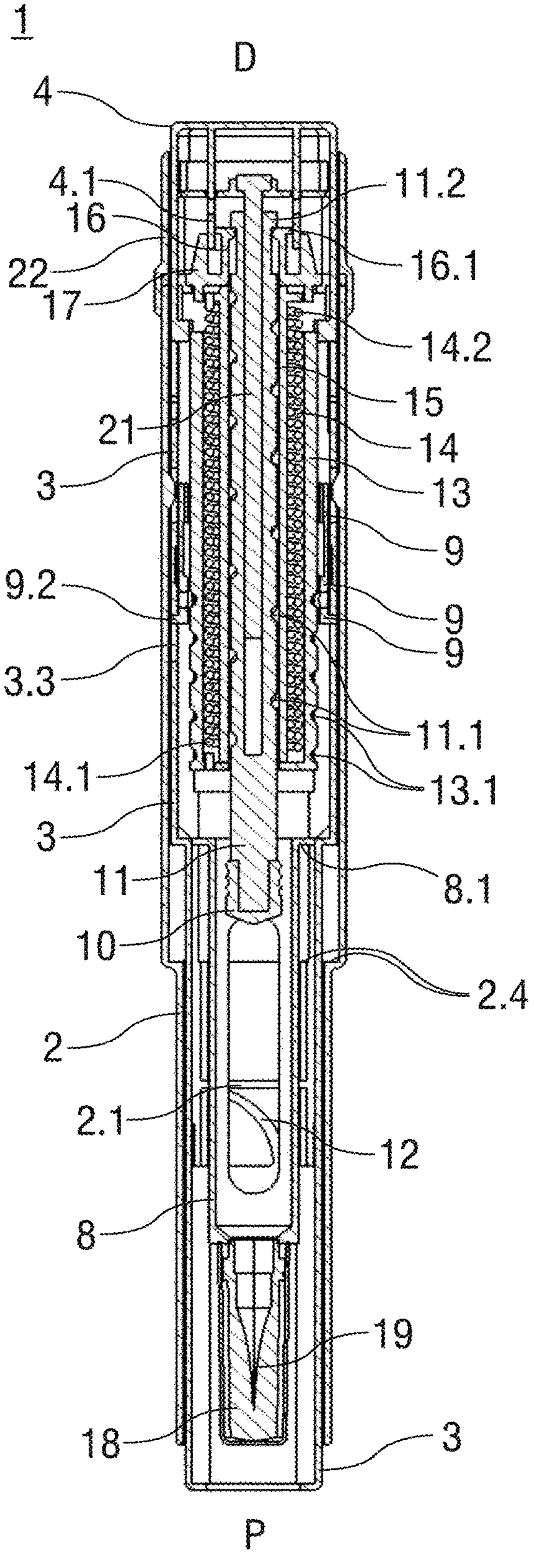
FIGS. 2A-B show longitudinal sections of the auto-injector in an initial state.
Figure 2B:
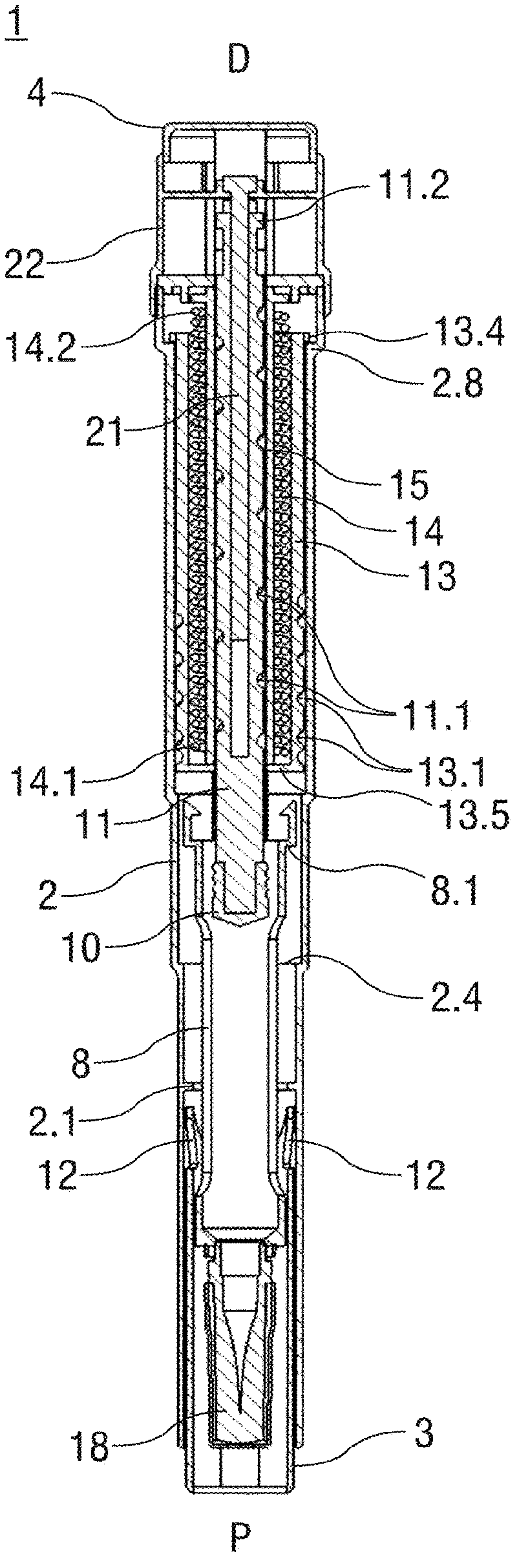

FIGS. 2*a* and 2*b* are longitudinal sections of the auto-injector 1 in different section planes approximately 90° offset from each other. The auto-injector 1 is in an initial state prior to use. A syringe 7 is partially surrounded and supported at a front end by a syringe carrier 8. Attached at the front end of the syringe 7 is a hollow injection needle 19 for piercing a patient's skin and delivering a liquid medicament stored inside the syringe 7 (syringe and needle are not shown in FIG. 2*b* for clarity). Near the distal end of the syringe 7 a stopper 10 is arranged for sealing and containing the medicament. The stopper 10 may be advanced by a plunger 11 (e.g., a second gear member of a second gear arrangement) in order to expel the medicament M from the syringe 7. The syringe carrier 8 is slidably arranged inside the needle shroud 3. The needle shroud 3 is biased towards a proximal end P by a shroud spring 12 in the shape of an integral compliant polymer beam element integrally moulded with the needle shroud 3 and acting against a first rib 2.1 in the housing 2. The shroud spring 12 could likewise be of a different type, e.g. a compression spring.

The plunger 11 exhibits an external plunger lead screw 11.1 and is rotationally fixed to the housing 2 by a torque reaction rod 21 arranged in an axial bore of the plunger 11. The axial bore and the torque reaction rod 21 both have a non-circular profile in order to keep the plunger 11 from rotating, e.g. a square profile or a profile with at least one spline or flat. The torque reaction rod 21 is attached to the housing 2 at the distal end D of the auto-injector 1 through a framework in a distal end cap 22 in such a manner that the torque reaction rod 21 is prevented from rotating relative to the housing 2.

The plunger 11 is arranged inside a tubular plunger follower 15 (e.g., a first gear member of the second gear arrangement), which is engaged to the plunger lead screw 11.1 by at least one ball bearing (not illustrated). The plunger follower 15 is arranged inside a torsion spring 14 which in turn is arranged inside a tubular shroud lead screw 13 (e.g., a first gear member of a first gear arrangement) with an external shroud lead screw thread 13.1. A tubular shroud follower 9 (e.g., a second gear member of the first gear arrangement) is arranged around the shroud lead screw 13 and inside a distal part of the needle shroud 3. The shroud follower 9 is engaged to the shroud lead screw 13 by at least one ball bearing (not illustrated).

The extension of the needle shroud 3 from the proximal end P is limited by engagement of a pin 9.2 on the shroud follower 9 in a slot hole 3.3 in the needle shroud 3. This engagement also fixes the shroud follower 9 rotationally to the needle shroud 3. The shroud follower 9 is axially fixed to the tubular shroud lead screw 13 by the ball bearing.

Figure 4:
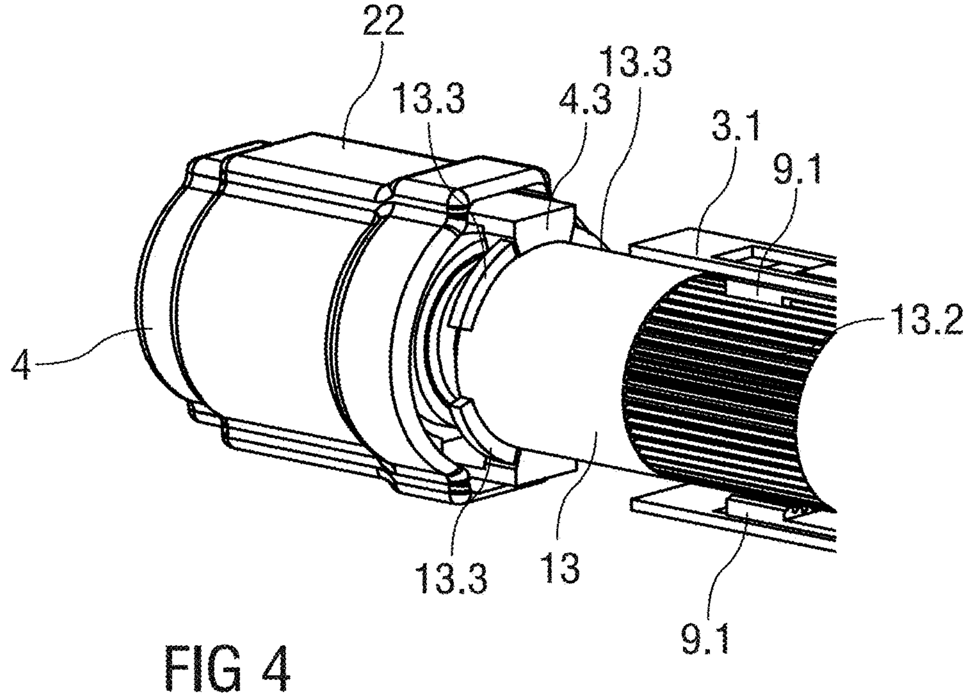
FIG. 4 is a detail view of a distal end of the auto-injector with a trigger button in the situation as in FIG. 3.

Axial translation of the shroud lead screw 13 in the proximal direction P is prevented by an external lip 13.4 on the distal end of the shroud lead screw 13 abutting against a step 2.8 in the housing 2. Axial translation of the shroud lead screw 13 in the distal direction D is prevented by an internal flange 13.5 distally bearing against the proximal end of the plunger follower 15. The plunger follower 15 is axially fixed to the housing 2 at its distal end. In the initial state, rotation of the shroud lead screw 13 is prevented by splined engagement with the trigger button 4 (see FIG. 4). For this purpose the trigger button 4 has an inward boss 4.3 engaged between circumferential outward bosses 13.3 on the shroud lead screw 13.

The torque from the proximal end 14.1 of the torsion spring 14 is resolved into the shroud lead screw 13. The torque from the distal end 14.2 is resolved into the plunger follower 15. The torque from the plunger follower 15 is coupled through the ball bearing into an axial force in the plunger 11. In the initial state, axial loads within the plunger 11 are resolved through into the housing 2 by means of a chassis clip arrangement at the distal end D. The chassis clip arrangement comprises two resilient chassis clips 16 fixed to the housing 2. The chassis clips 16 are engaged proximally behind a shoulder 11.2 in the plunger 11 in a manner to prevent translation of the plunger 11 in proximal direction P. Due to ramped engagement the shoulder 11.2 is trying to flex the chassis clips 16 outwards which is prevented by two trigger beams 4.1 on the trigger button 4 respectively arranged between an outward pin on the chassis clip 16 and a rigid support beam 17.

Figure 5:
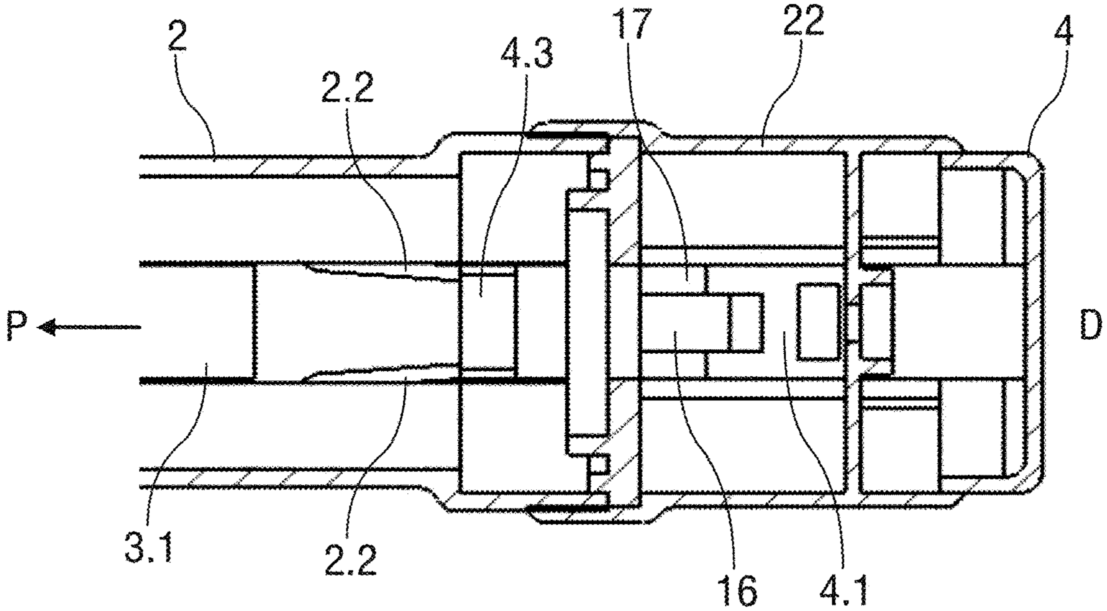
FIG. 5 is a detail view of the trigger button with an interlock feature to a needle shroud in the situation as in FIG. 3.
Figure 8:
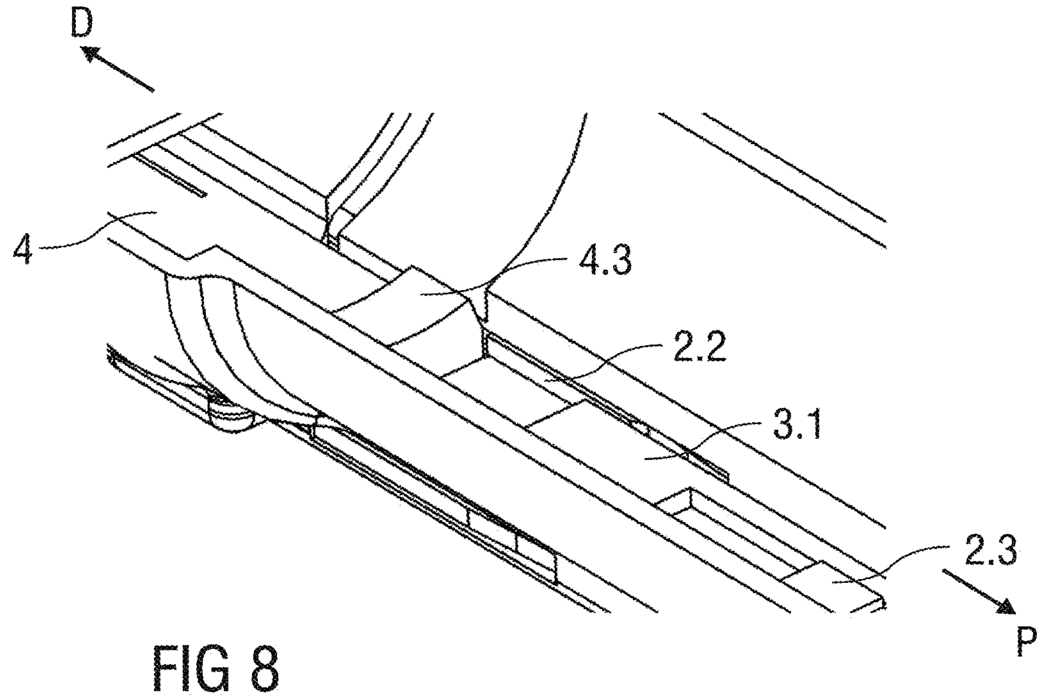
FIG. 8 is an isometric detail view of the interlock feature of FIG. 5 disengaged by depression of the needle shroud.
Figure 9:
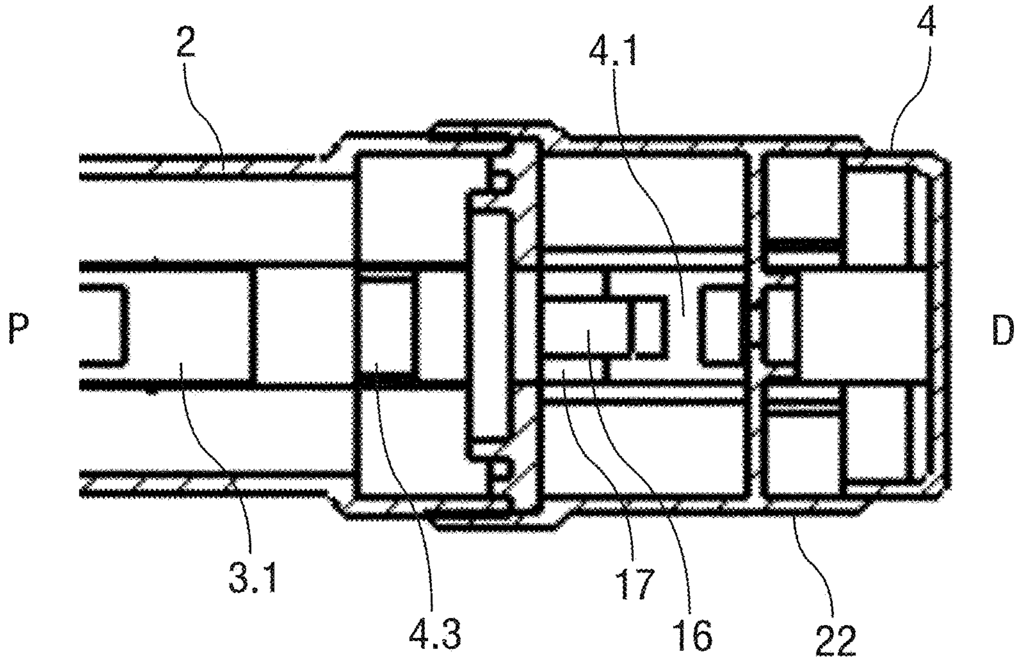
FIG. 9 is a longitudinal section of the detail view of FIG. 8.
Figure 10:
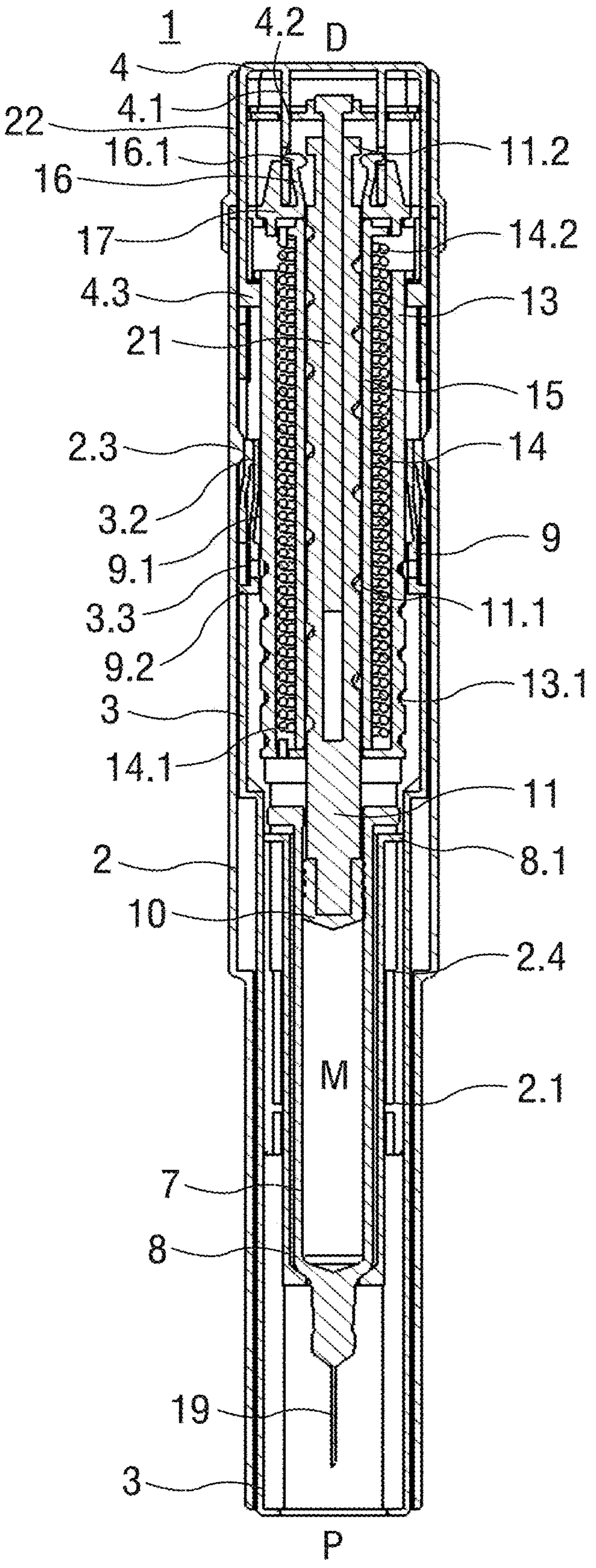
FIG. 10 is a longitudinal section of the auto-injector after depression of the trigger button.
Figure 11:
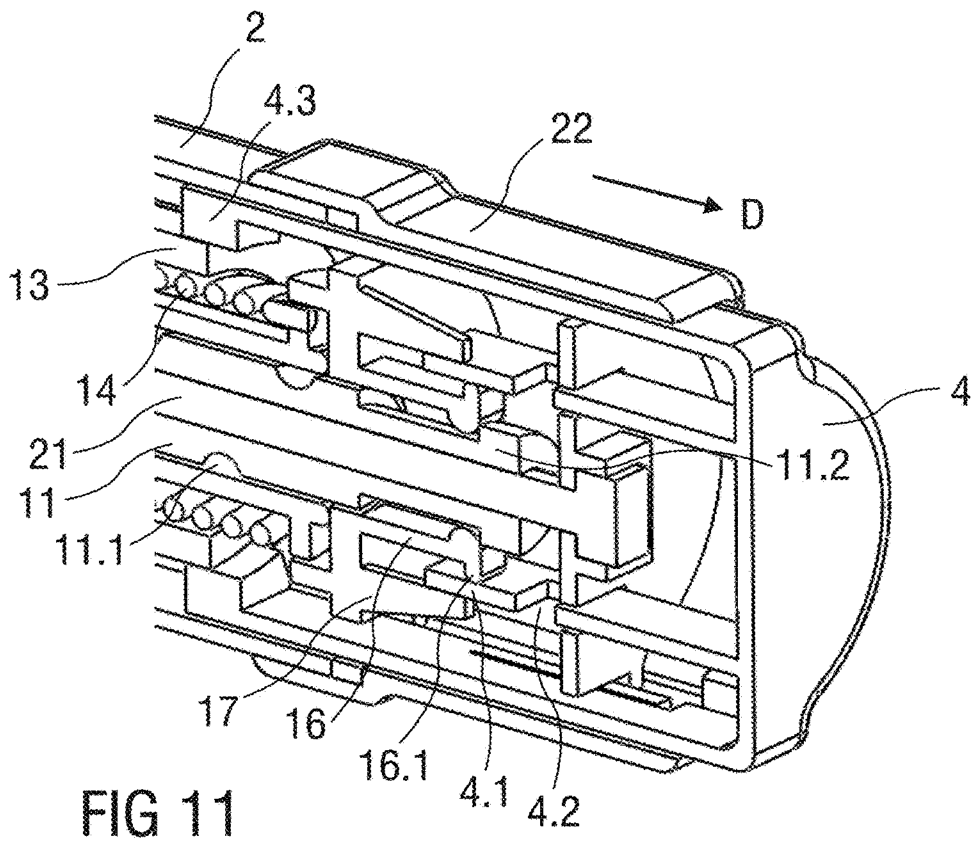
FIG. 11 is an isometric detail view of the trigger button prior to depression of the trigger button.
Figure 12:
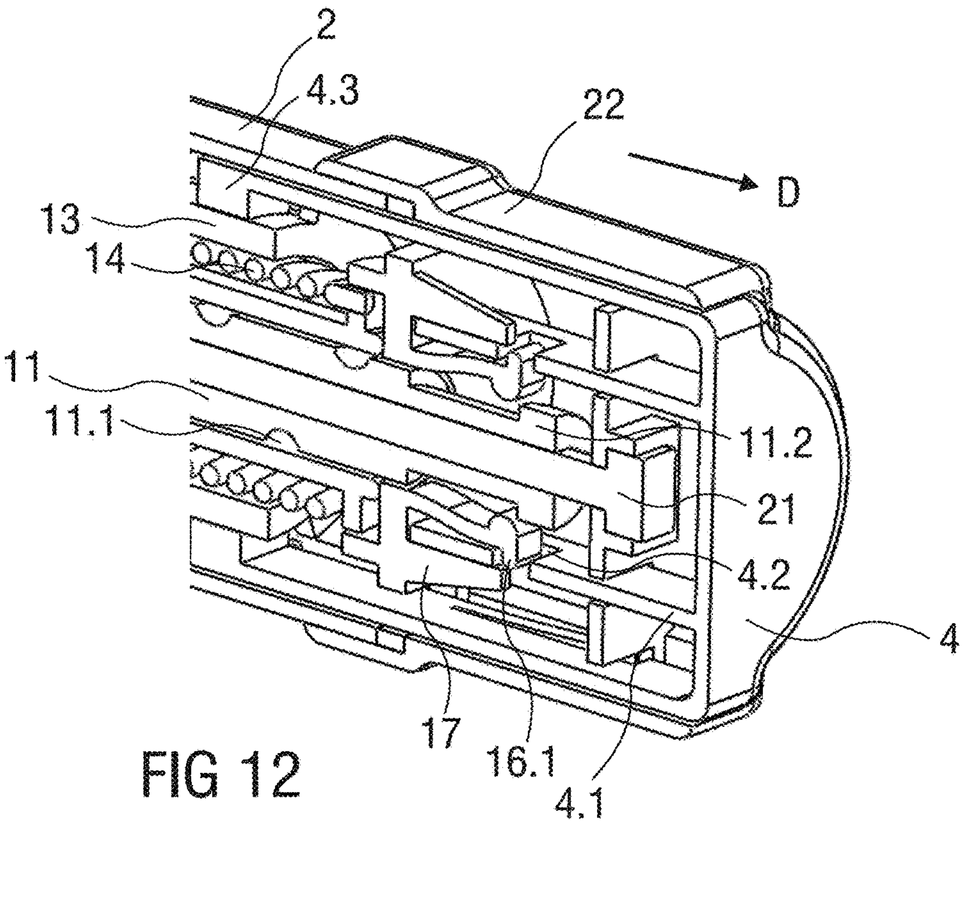
FIG. 12 is an isometric detail view of the trigger button after depression of the trigger button.
Figure 13:
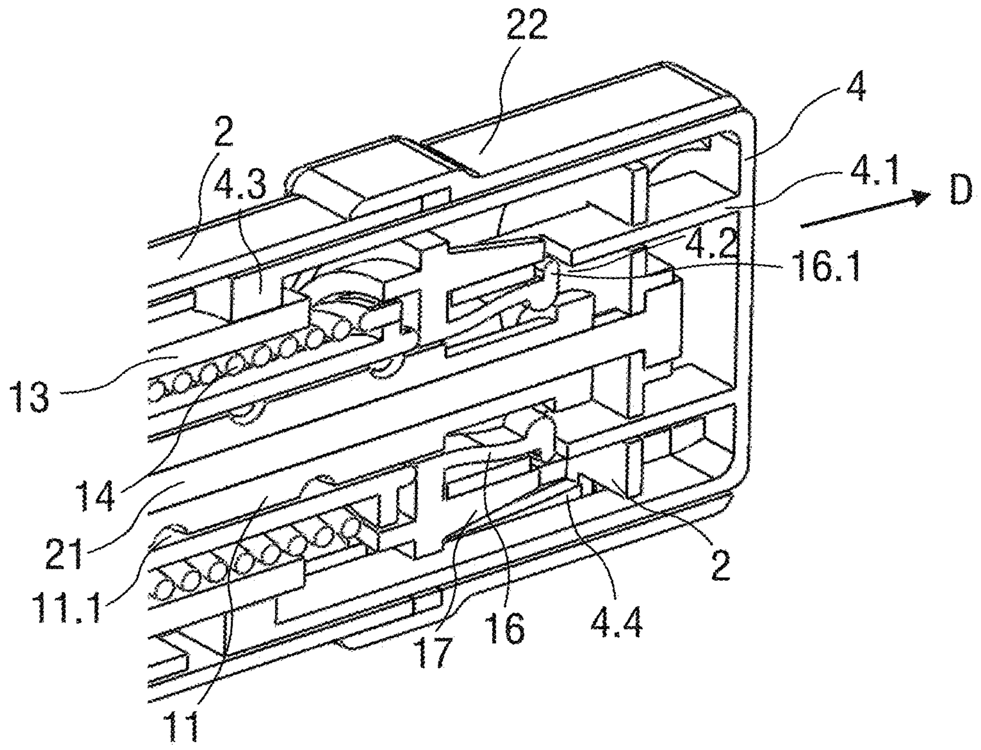
FIG. 13 is another isometric detail view of the trigger button after depression of the trigger button.
Figure 14:
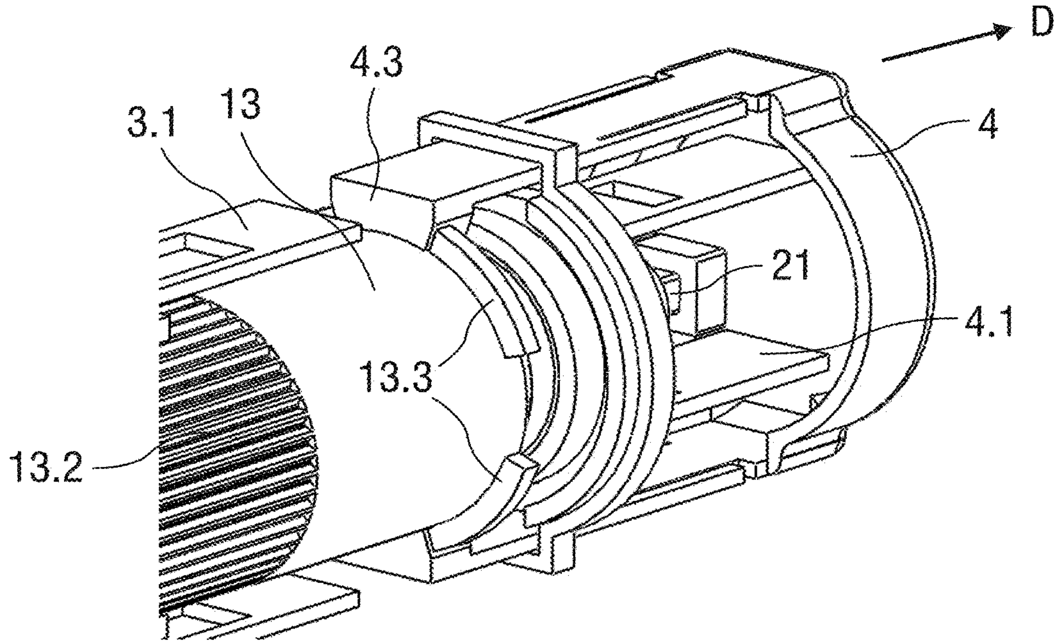
FIG. 14 is another isometric detail view of the trigger button prior to depression of the trigger button.
Figure 15:
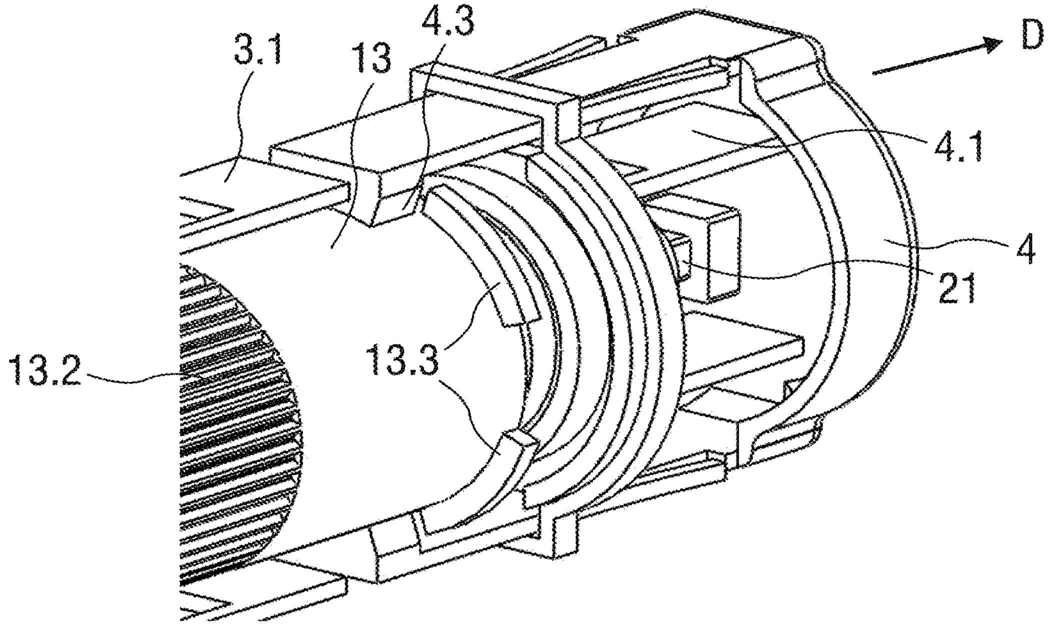
FIG. 15 is yet another isometric detail view of the trigger button after depression of the trigger button.

The trigger button 4 is locked in a distal position in the initial state to prevent unintended activation of the auto-injector 1. Flexible first beam elements 2.2 integrally moulded with the housing 2 obstruct the motion of the trigger button 4 if attempts are made to depress it (see FIGS. 5, 8). The first beam elements 2.2 are deflected out of the path of the trigger button 4 by a second beam element 3.1 on the needle shroud 3 on axial movement of the needle shroud 3 within the housing 2 (see FIGS. 8, 9) in distal direction D. This is achieved when the proximal end P is pressed against the injection site.

In the as delivered initial state a protective needle shield 18 is arranged on the injection needle 19.

Figure 3:
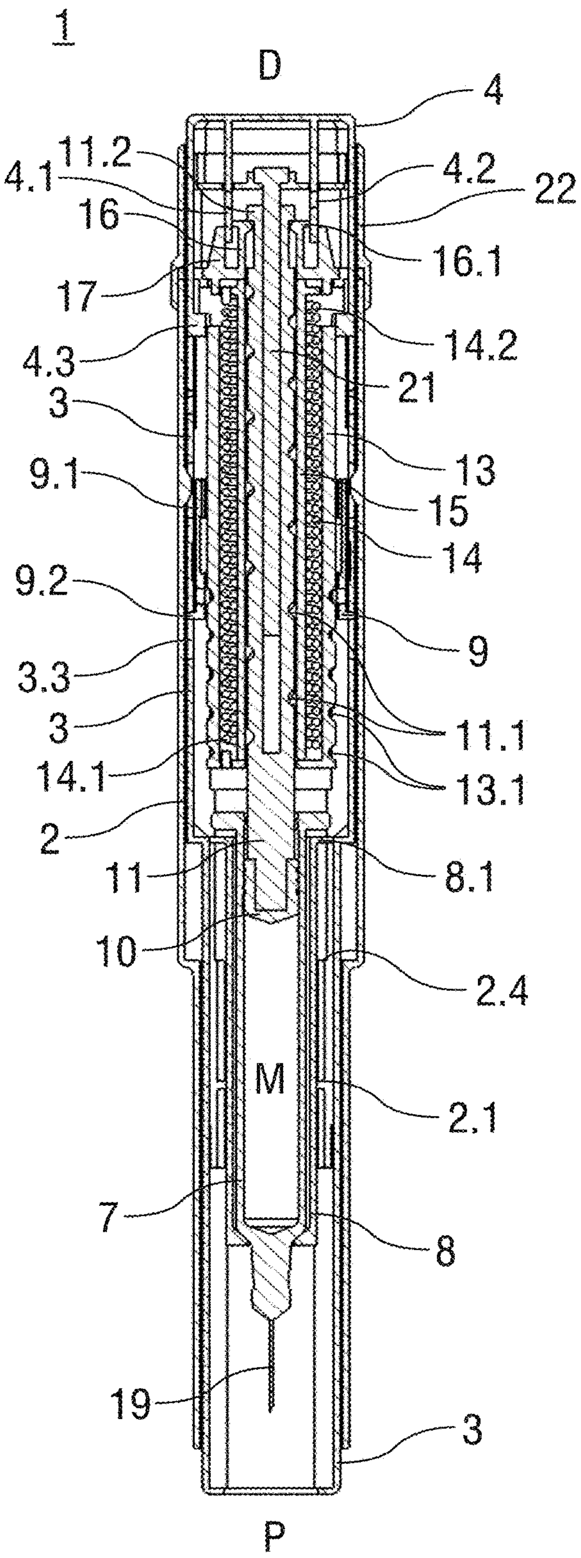
FIG. 3 is a longitudinal section of the auto-injector after removal of a protective needle shroud.

A sequence of operation is as follows:

The user removes the protective needle shield 18 from the needle 19. This can be achieved by a device cap engaged with the needle (not illustrated). The needle 19 is a safe distance back within the needle shroud 3 to protect the user from accidental needle stick injuries (see FIG. 3).

Figure 6:
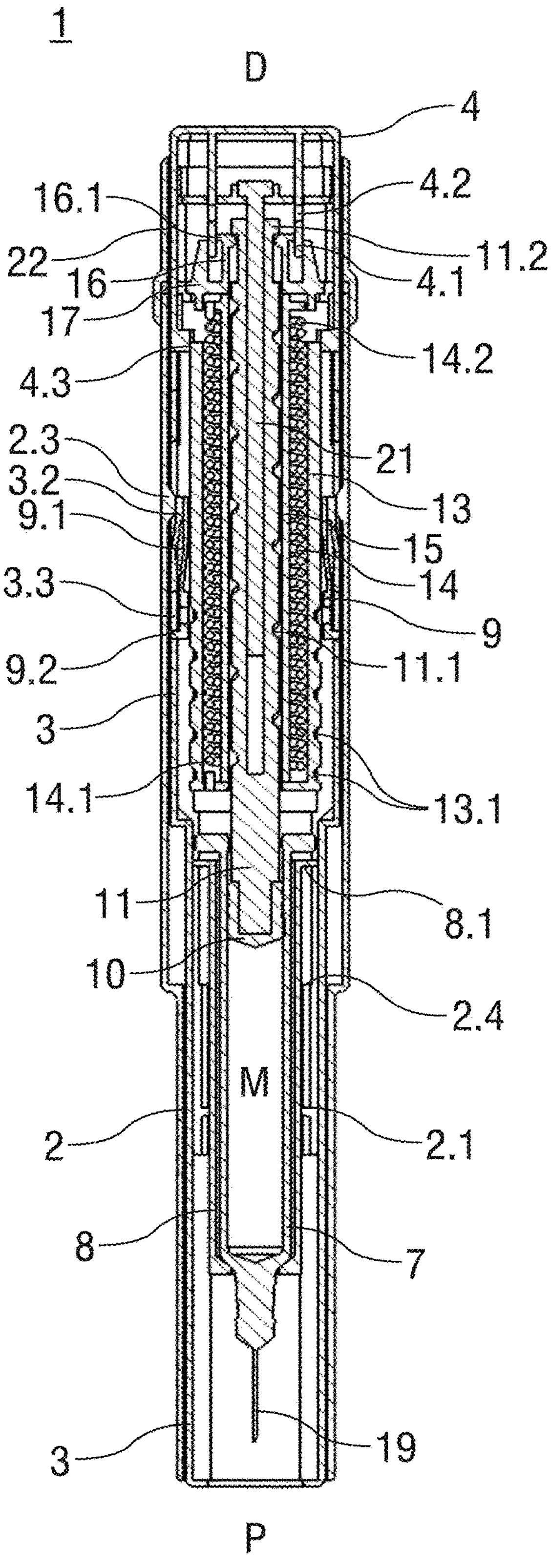
FIG. 6 is a longitudinal section of the auto-injector after depression of the needle shroud.
Figure 7:
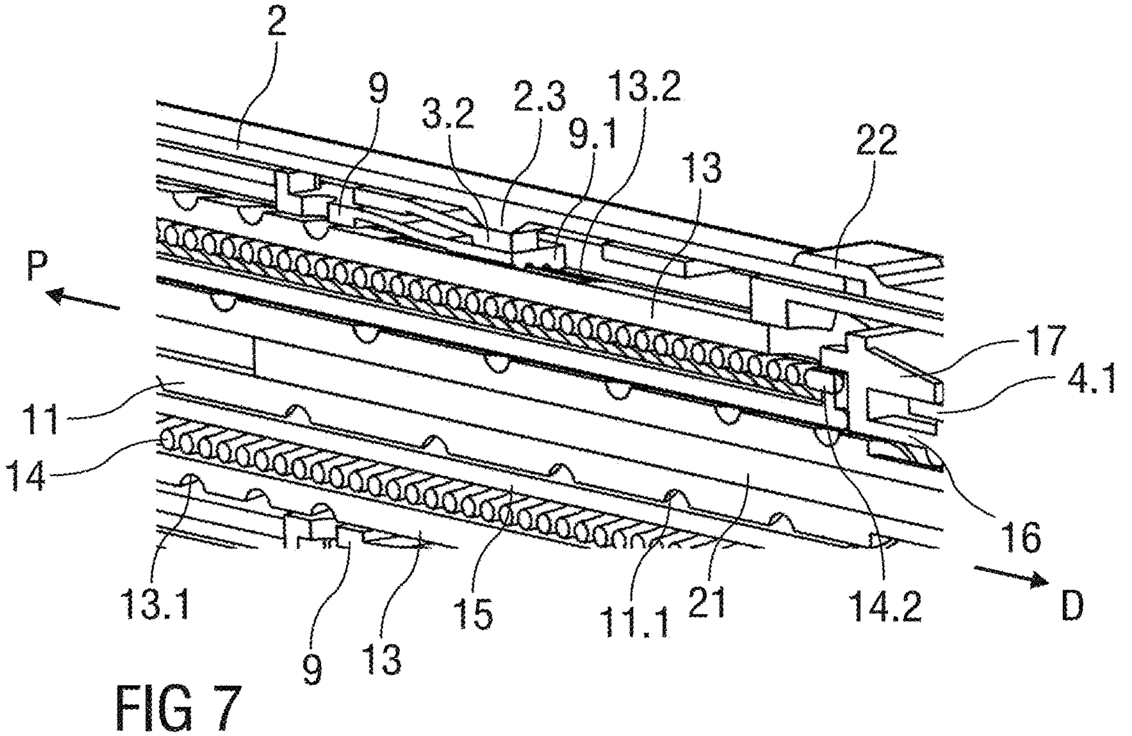
FIG. 7 is an isometric detail view of a shroud follower locked in rotation to a shroud lead screw by depression of the needle shroud.

The user places and pushes the proximal end P of the auto-injector 1 on the injection site, e.g. a patient's skin. The needle shroud 3 moves in distal direction D into the housing 2 by a small distance (see FIG. 6). Due to the slot hole 3.3 this translation does not translate the shroud follower 9. The translating second beam element 3.1 flexes the first beam elements 2.2 outwards thus clearing the path for the trigger button 4 and releasing the aforementioned interlock (see FIGS. 8, 9). The moulded shroud spring 12 opposes this motion but is specified such that its spring rate and preload are low enough for this to feel natural. A resilient third beam element 3.2 on the needle shroud 3 is deflected inwards by contact with a ramped second rib 2.3 on the housing 2 on translation of the needle shroud 3. The third beam element 3.2 deflects a fourth beam element 9.1 on the shroud follower 9 into a spline 13.2 on the shroud lead screw 13 (see FIGS. 4, 7).

As the shroud follower 9 is rotationally fixed to the housing 2 through its engagement with the needle shroud 3, the fourth beam element 9.1 provides further grounding of the shroud lead screw 13 to the housing 2. As detailed above, the shroud lead screw 13 is already grounded to the housing 2 through a splined engagement with the trigger button 4.

When ready to do so, the user depresses the trigger button 4, translating it in proximal direction P (see FIGS. 10, 12, 13, 15). The trigger beams 4.1 on the trigger button 4 are translated with the trigger button 4 in a manner to allow the outward pin 16.1 to enter an aperture 4.2 in the trigger beam 4.1 by the chassis clip 16 being flexed outwards due to ramped engagement with the shoulder 11.2 under the force pulling the plunger 11 in proximal direction P.

The plunger 11 moves in proximal direction P towards the stopper 10 driven by rotation of the plunger follower 15. As stated, the plunger 11 is prevented from rotating by the torque reaction rod 21 down its centre. This could be achieved with one or more splines, flats or by using a square shaft as shown in this embodiment. One or more ball bearings provide a low friction contact between the plunger follower 15 and the plunger lead screw 11.1. Depression of the trigger button 4 also removes the splined engagement of the trigger button 4 from the shroud lead screw 13 by translating the inward boss 4.3 out of engagement with the circumferential outward bosses 13.3 (see FIG. 15). Now, the shroud lead screw 13 is grounded to the housing 2 through the shroud follower 9 only. This means at any point from now, a shroud extension mechanism described below would be triggered if the auto-injector 1 is removed from the injection site, thereby ensuring the needle 19 is covered. The trigger button 4 is locked in a fully depressed position by snaps 4.4 acting against the housing 2 (see FIGS. 13 and 15).

Figure 16:
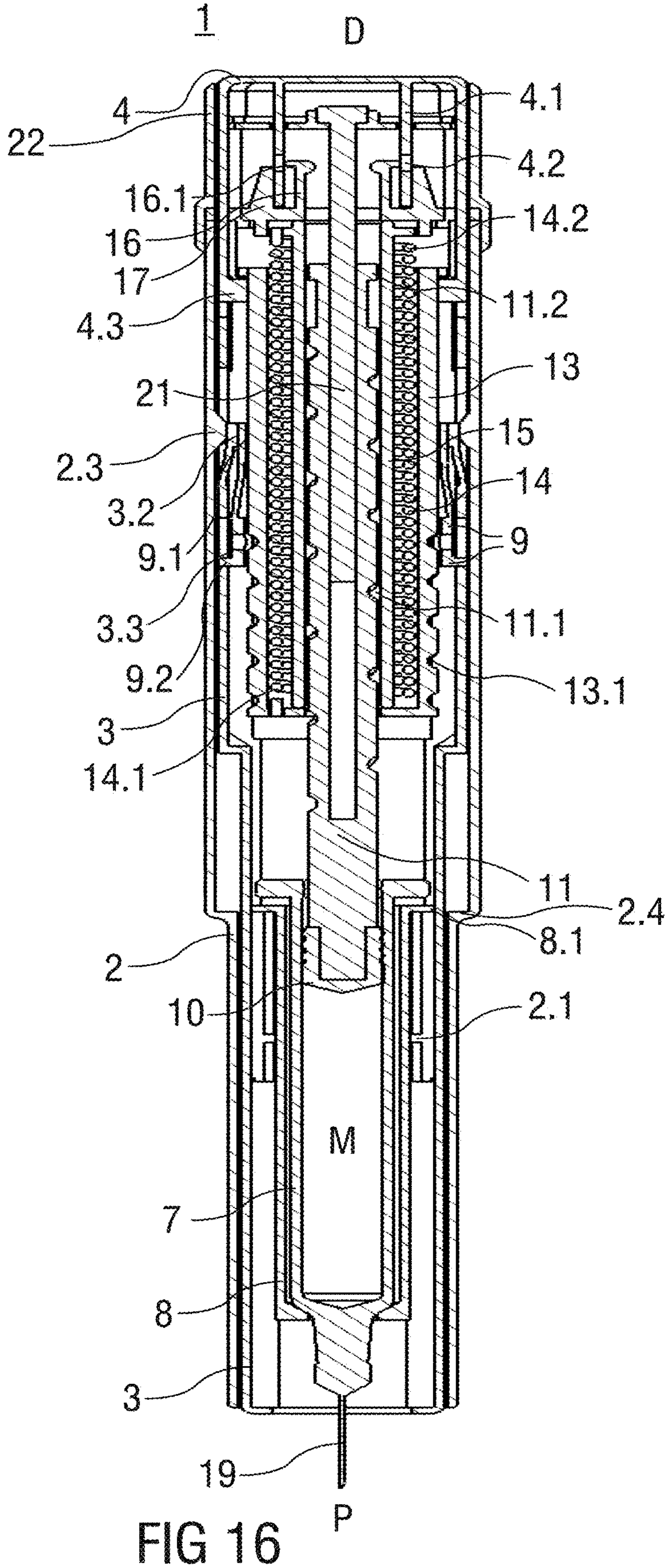
FIG. 16 is the auto-injector with a syringe advanced for needle insertion.
Figure 17:
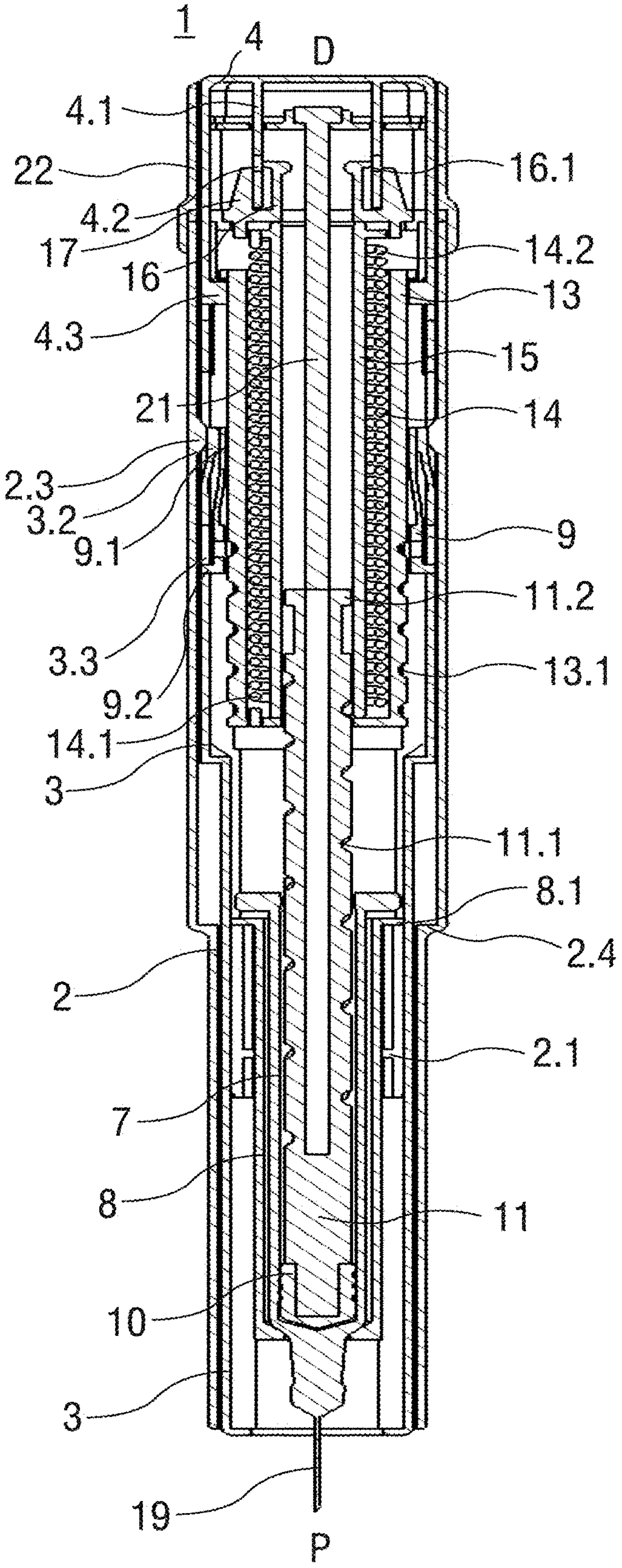
FIG. 17 is the auto-injector with the emptied syringe.

The plunger 11 drives the syringe 7 forward by pushing on the stopper 10 thus inserting the needle 19 into the injection site. The subcutaneous injection depth is set by a rear flange 8.1 on the syringe carrier 8 contacting a stop 2.4 in the housing 2 (see FIG. 16).

When the injection depth has been reached the stopper 10 is driven forwards in proximal direction P within the syringe 7, injecting the dose of medicament M. The stopper 10 continues to move until it reaches the end of the syringe 7 thereby fully emptying the syringe 7. This would require the user to hold the auto-injector 1 in place for a sufficient period of time. In this embodiment, the user is asked to keep pressure on the injection site for a short period of time (e.g. approximately 10 seconds), which can be communicated to the user through user instructions. Other options would be observance of moving components within the auto-injector 1, or an audible ratchet detecting movement of the plunger 11.

Figure 18:
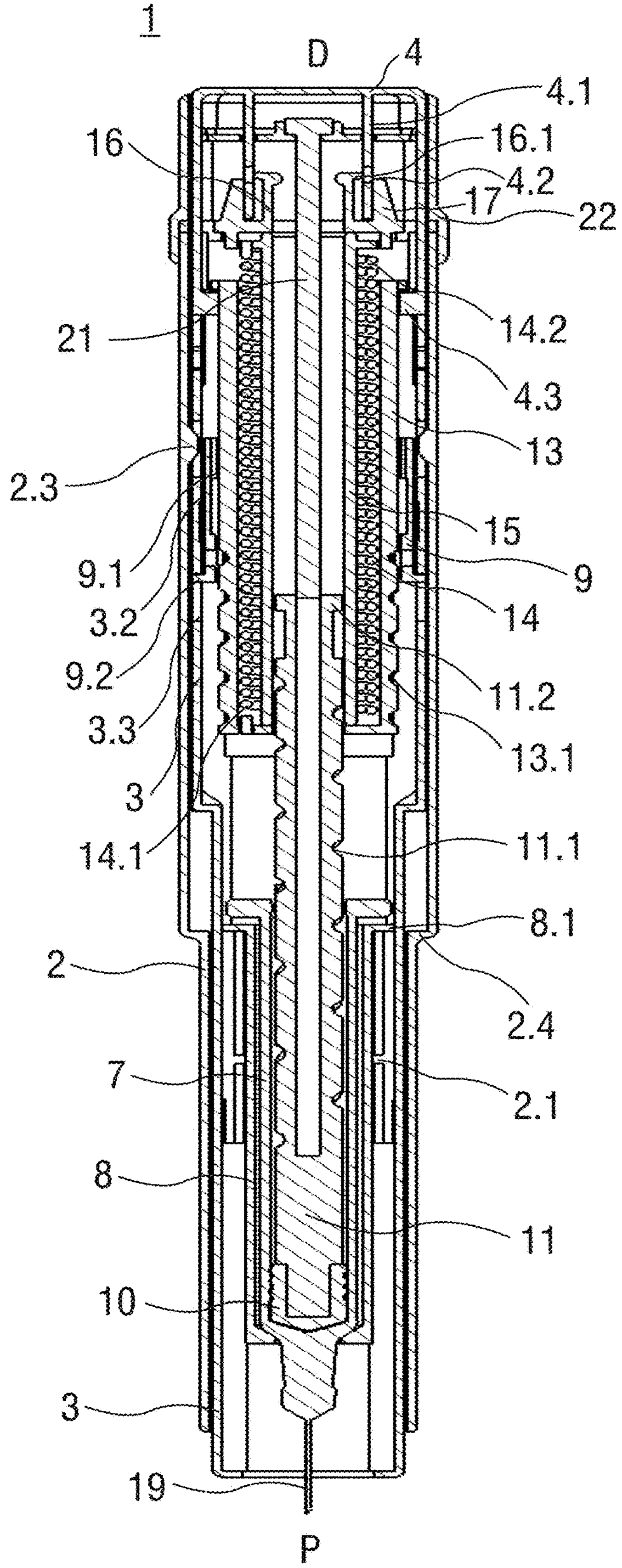
FIG. 18 is the auto-injector on removal from the injection site after the syringe has been emptied.
Figure 19:
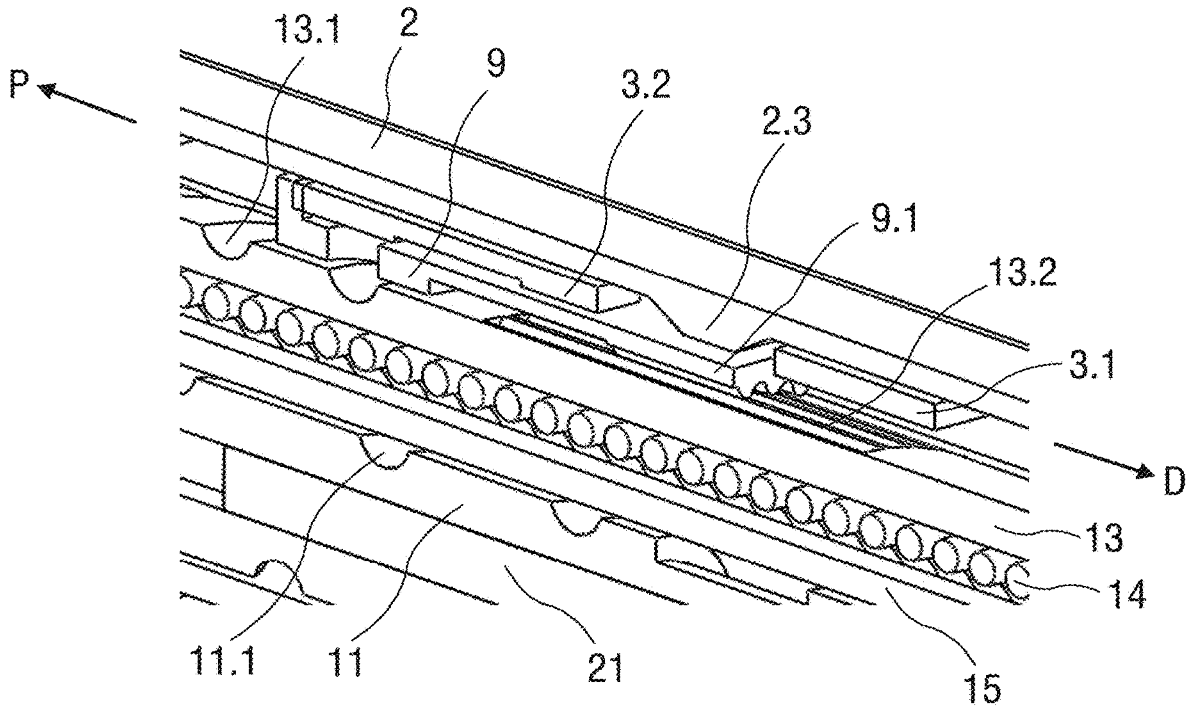
FIG. 19 is a detail view in the situation as in FIG. 18 with the shroud lead screw released for rotation.
Figure 20:
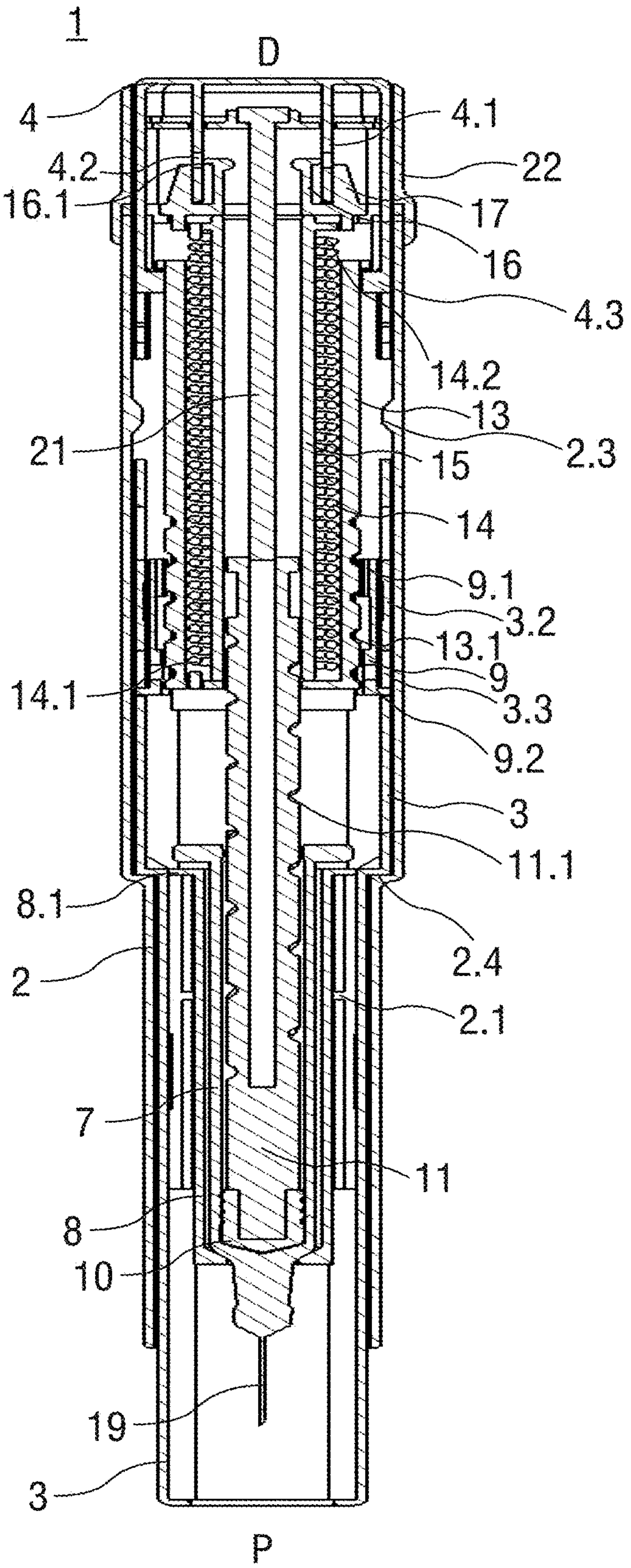
FIG. 20 is the auto-injector with the needle shroud fully advanced for post injection needle safety.
Figure 21:
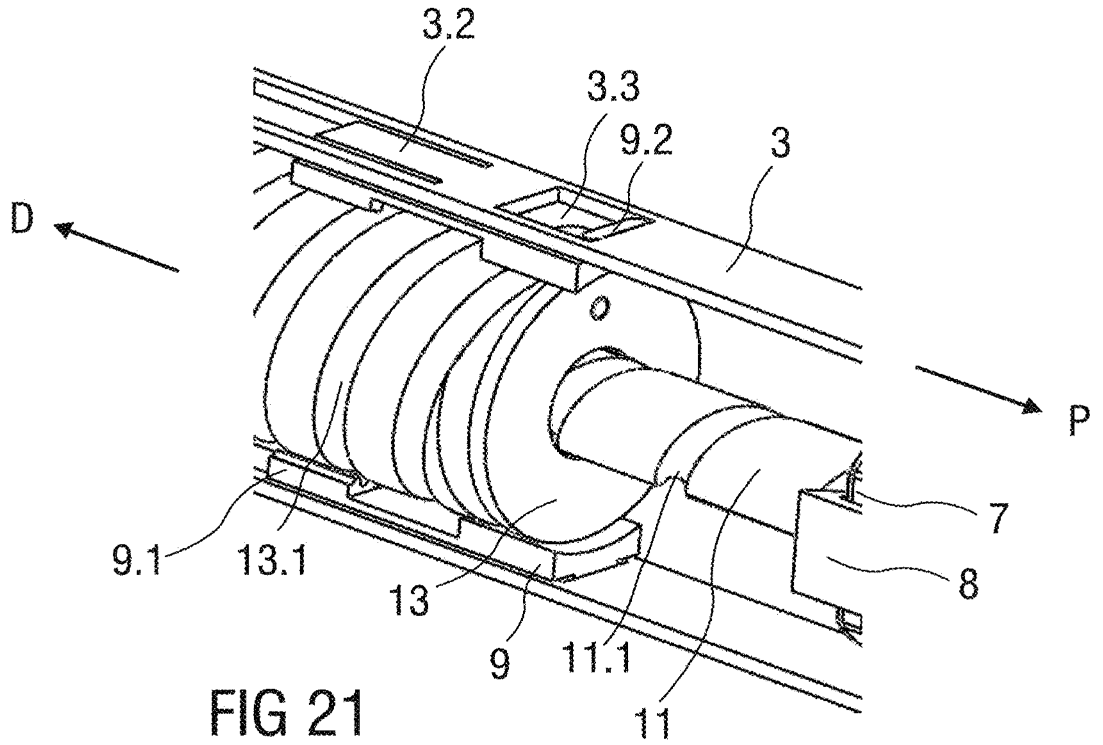
FIG. 21 is a detail view of the shroud lead screw in the situation as in FIG. 20.

After confirmation that the full dose has been delivered, the user withdraws the auto-injector 1 from the injection site. With withdrawal, the needle 19 is extracted from the skin, and the needle shroud 3 extends under the force of the shroud spring 12 (see FIG. 18). The third beam element 3.2 is translated back in proximal direction P thus no longer deflecting the fourth beam element 9.1 inwards. Hence the fourth beam element 9.1 flexes outwards again and disengages the shroud follower 9 from the shroud lead screw 13. Therefore torque within the shroud lead screw 13 is no longer resolved through to the housing 2 (see FIG. 19). With the grounding to the housing 2 removed, the torque is now resolved through the ball bearing interface to an axial force on the shroud follower 9. Further movement of the plunger 11 in the proximal direction P is not possible in this situation, so when the shroud follower 9 is released it moves in the proximal direction P pushing the needle shroud 3 further out of the proximal end P of the housing 2 thus completely covering the needle 19 (see FIG. 20). The shroud lead screw thread 13.1 ends with a pitch of zero on the proximal end allowing any remaining torque in the torsion spring 14 to be released (see FIG. 21). This makes the auto-injector 1 tamper proof post injection, e.g. if the user tries to dismantle the auto-injector 1.

Figure 22:
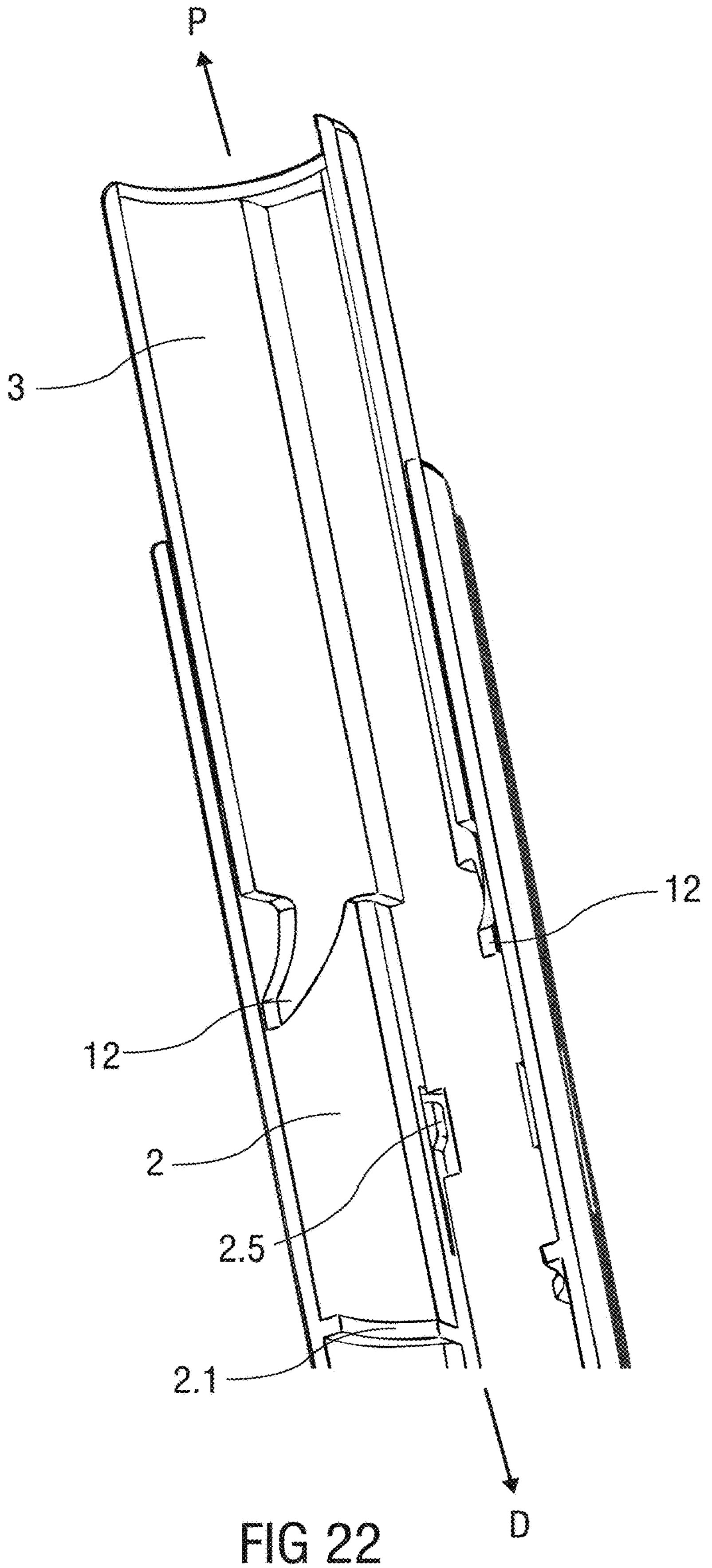
FIG. 22 is a detail view of the needle shroud locked in the position as in FIG. 20.

The needle shroud 3 is locked in this extended position by snaps 2.5 within the case 2 (see FIG. 22).

Figure 23:
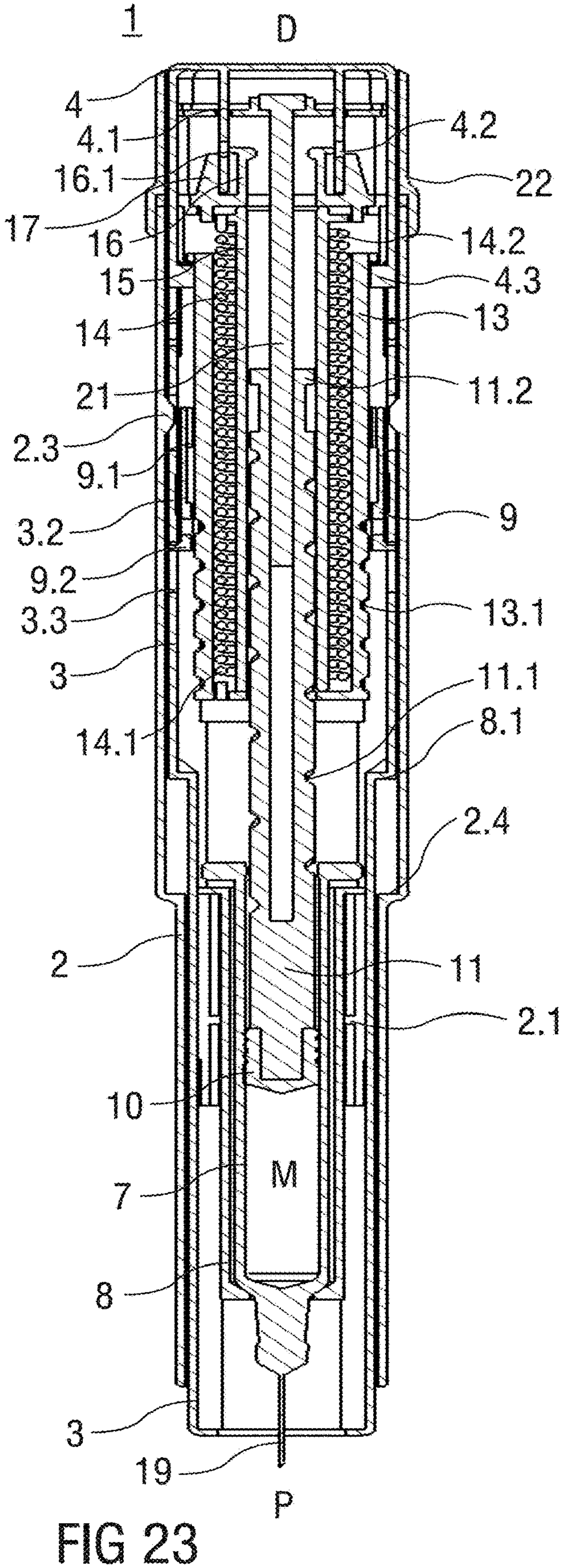
FIG. 23 is the auto-injector on removal from the injection site before the syringe has been emptied.

FIG. 23 illustrates removal from skin mid injection with the syringe 7 only partially emptied. As the shroud follower 9 disengages from the shroud lead screw 13, the torque within the shroud lead screw 13 is no longer resolved through to the housing 2 but through the ball bearing interface to an axial force on the shroud follower 9. Although the torque from the distal end 14.2 of the torsion spring 14 is still resolved through the plunger 11, the torque required to extend the needle shroud 3 is less than the torque required to forward the plunger 11, hence the distal end 14.2 becomes ground.

Figure 24:
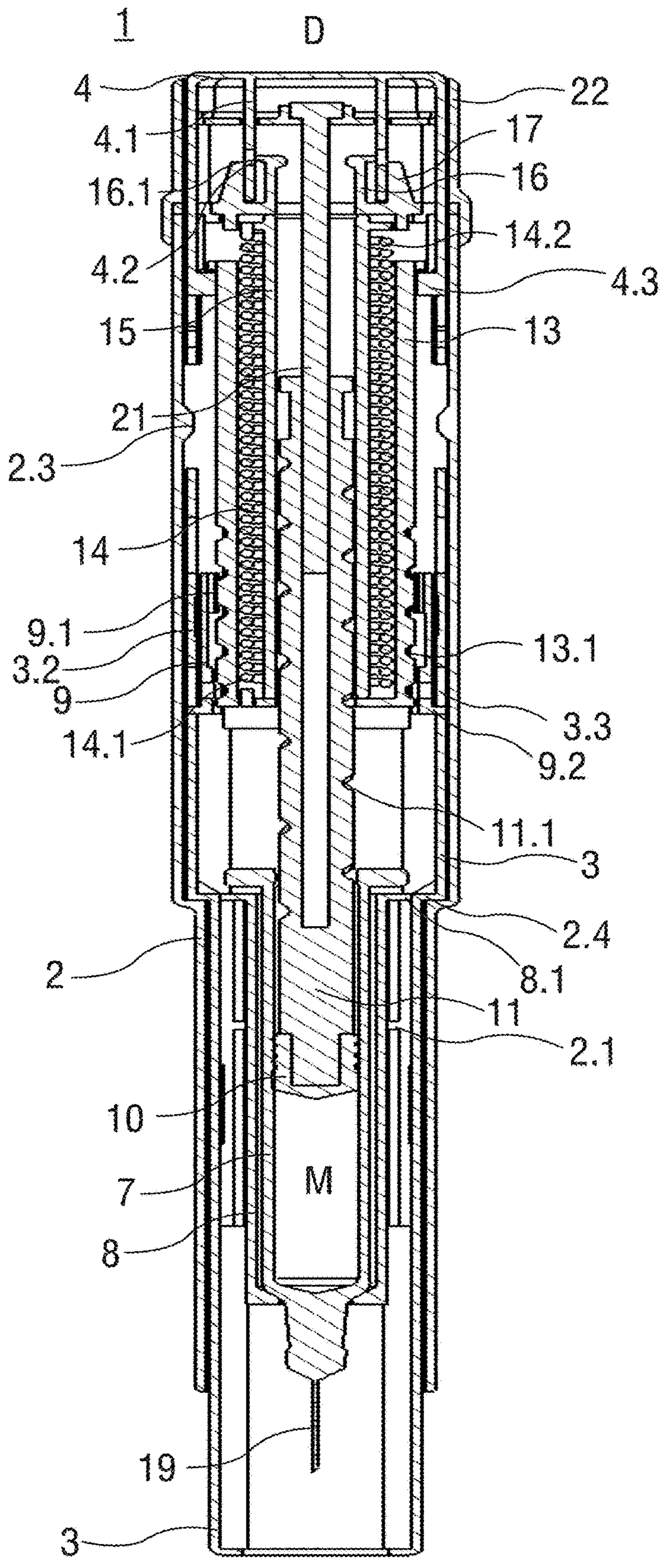
FIG. 24 is the auto-injector with the needle shroud fully advanced for post injection needle safety after delivery of a partial dose.

FIG. 24 shows the auto-injector 1 with the needle shroud 3 fully advanced for post injection needle safety after delivery of the partial dose. The zero end pitch of the shroud lead screw thread 13.1 allows the torsion spring 14 to be released preventing further drug delivery.

Figure 25:
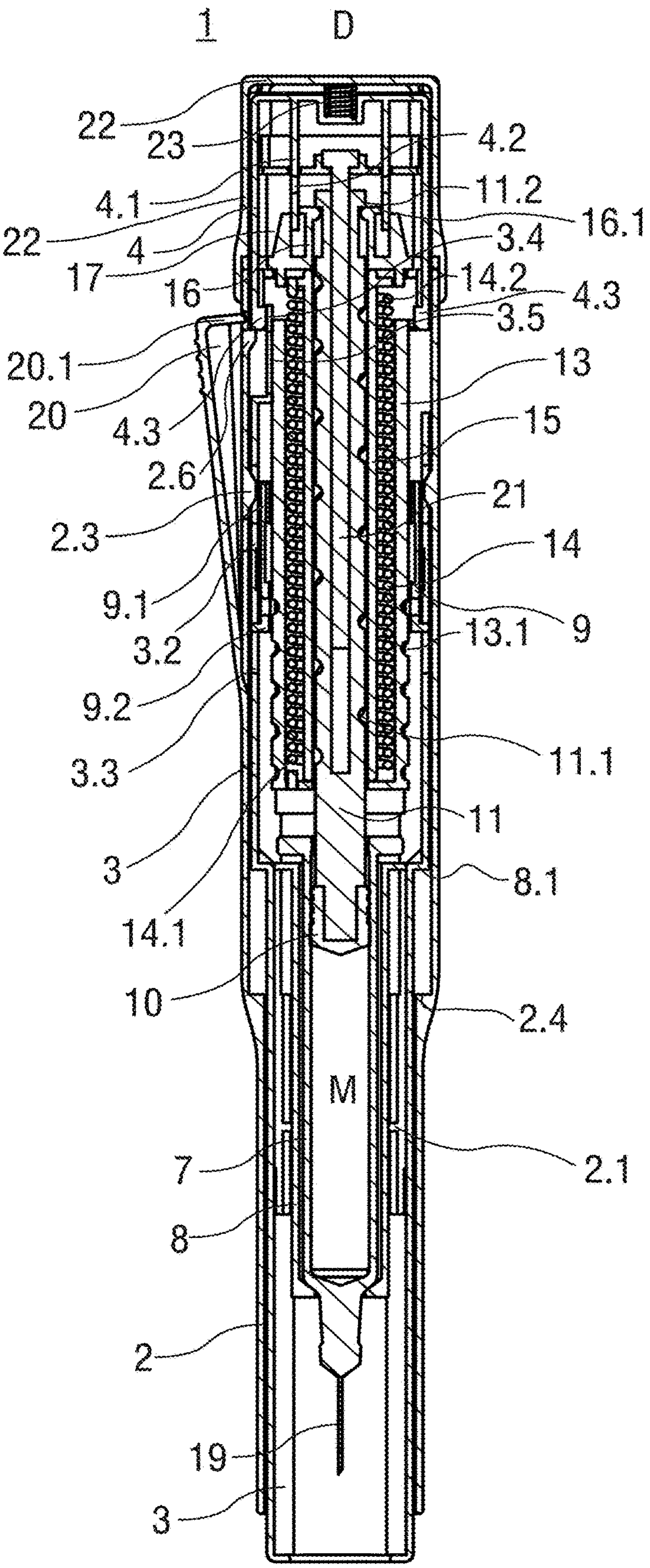
FIG. 25 is an alternative embodiment of the auto-injector with a lateral trigger button.

FIG. 25 shows an alternative embodiment of the auto-injector 1 with a lateral trigger button 20 (e.g., an activating member). The lateral trigger button 20 is an integral part of the housing 2. It may be moulded orthogonal to the housing 2 and then folded into place. However, the auto-injector 1 also comprises the end trigger button 4 of the embodiment illustrated in FIGS. 1 to 24, but hidden inside the distal end D closed by the distal cap 22 attached to the housing 2. A trigger spring 23 in the shape of a small compression spring applies a load between the distal cap 22 and the trigger button 4.

Figure 26:
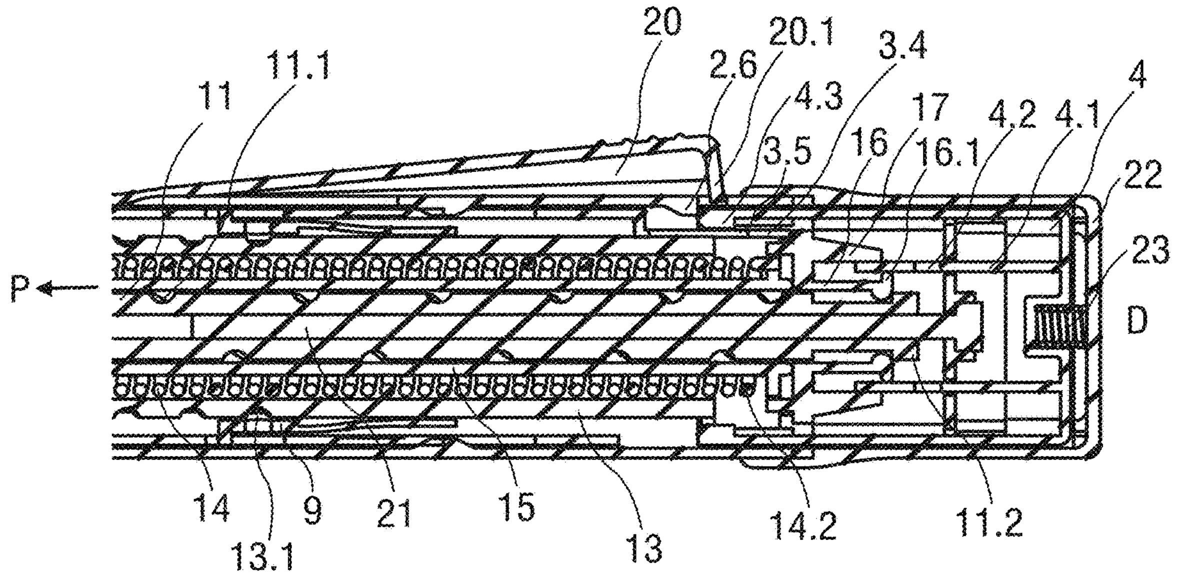
FIG. 26 is a detail view of an interlock mechanism between the lateral trigger button, the needle shroud and the end trigger button with the needle shroud depressed.
Figure 27:
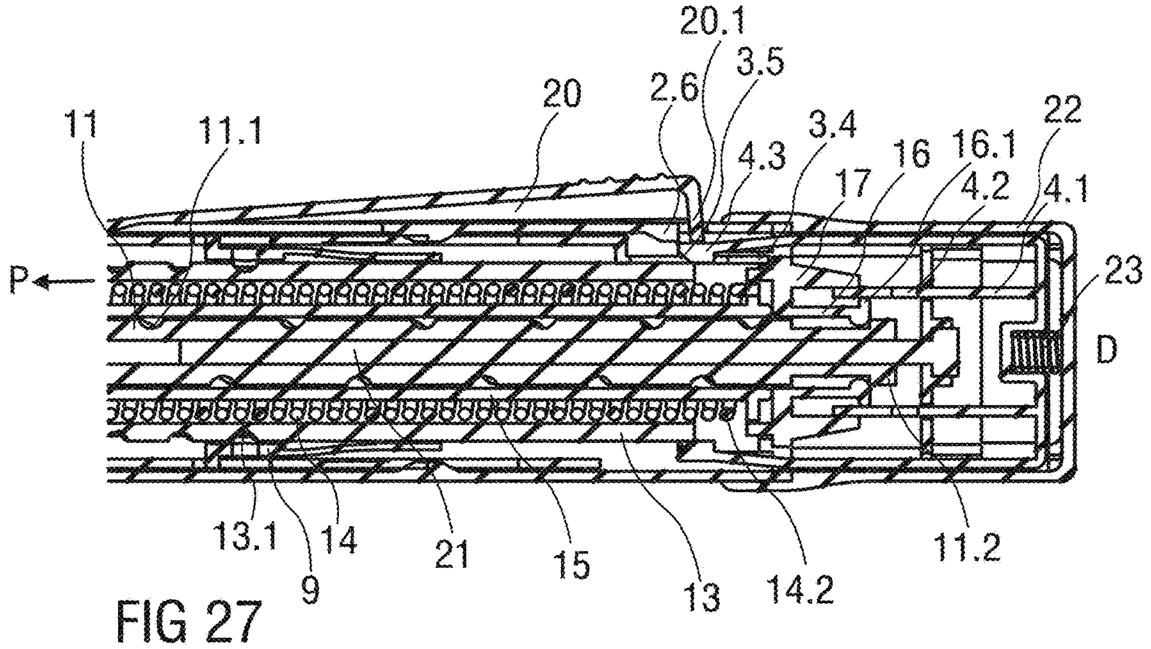
FIG. 27 is a detail view of the interlock mechanism with the lateral trigger button depressed and the end trigger button released.
Figure 28:
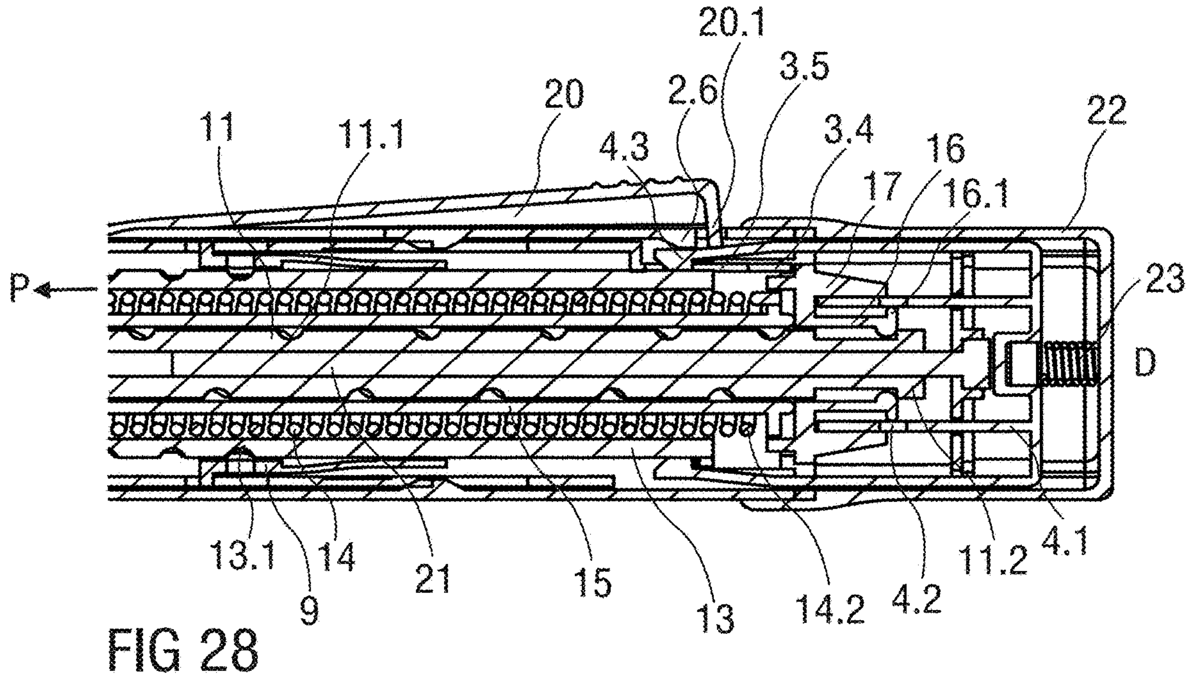
FIG. 28 is a detail view of the interlock mechanism with the end trigger button translated in proximal direction for releasing the plunger.

The sequence of operation is as described above for the embodiment in FIGS. 1 to 24 except in the following steps:

The initial position and function of all components is identical with the exception of the button interlock. The lateral trigger button 20 is locked in an extended position in the initial state to prevent unintended activation of the auto-injector 1. A boss 20.1 on the distal end of the lateral trigger button 20 extends through an aperture in the housing 2. In the initial state the boss 20.1 abuts against one of the inward bosses 4.3 on the end trigger button 4 which is inwardly supported by the shroud lead screw 13 and by a distal extension 3.4 on the needle shroud 3 arranged between the inward boss 4.3 and the shroud lead screw 13. Any force applied to the lateral trigger button 20 is therefore statically resolved preventing its depression. The inward boss 4.3 on the end trigger button 4 abuts against a third rib 2.6 in the housing 2 in proximal direction P thus preventing release of the end trigger button 4. When the auto-injector 1 is pressed against the skin, the needle shroud 3 translates within the housing 2 and a window 3.5 in the distal extension 3.4 becomes aligned with the boss 20.1 (see FIG. 26) allowing the lateral trigger button 20 to be depressed (see FIG. 27) thereby flexing the inward boss 4.3 inwards into the window 3.5 in such a manner that the inward boss 4.3 comes clear of the third rib 2.6 releasing the end trigger button 4 which is then translated under the action of the trigger spring 23 (see FIG. 28). This releases the chassis clip 16 resolving the axial load on the plunger 11 as in the embodiment in FIGS. 1 to 24.

Figure 29:
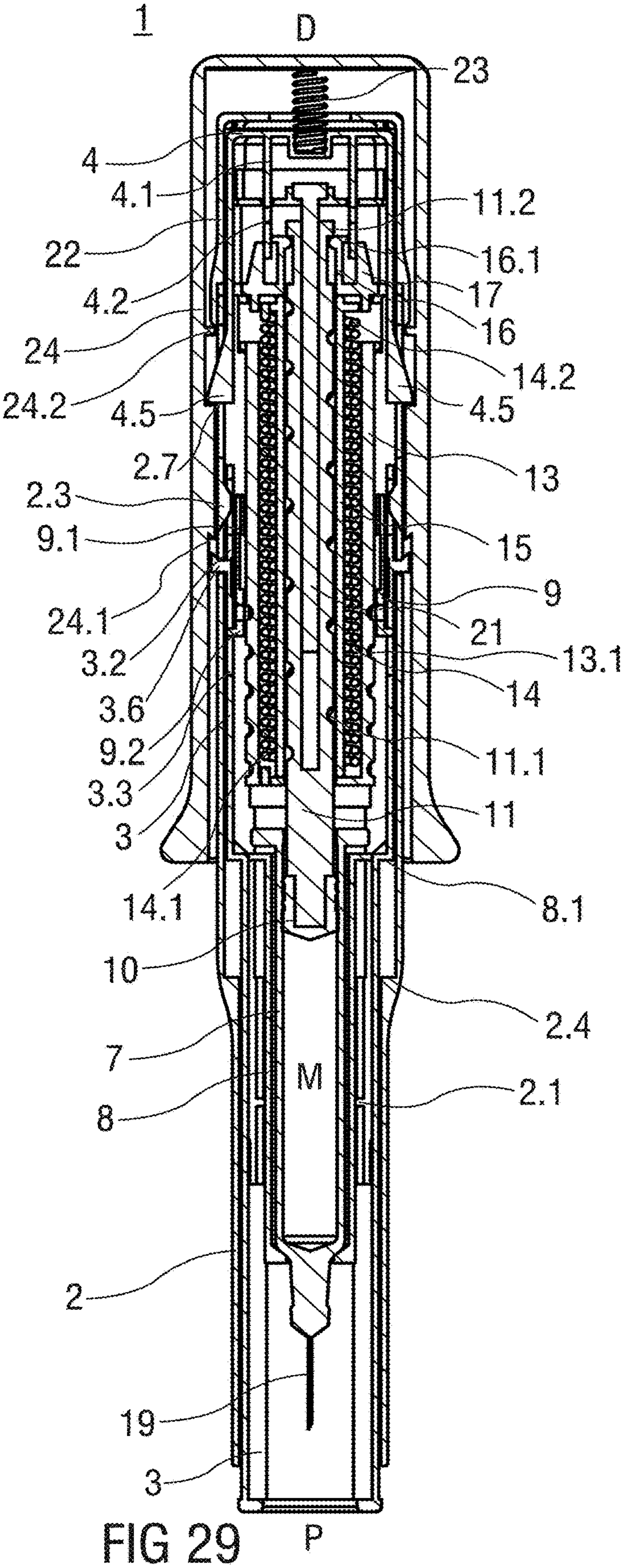
FIG. 29 is an alternative embodiment of the auto-injector with a wrap over sleeve trigger.
Figure 30:
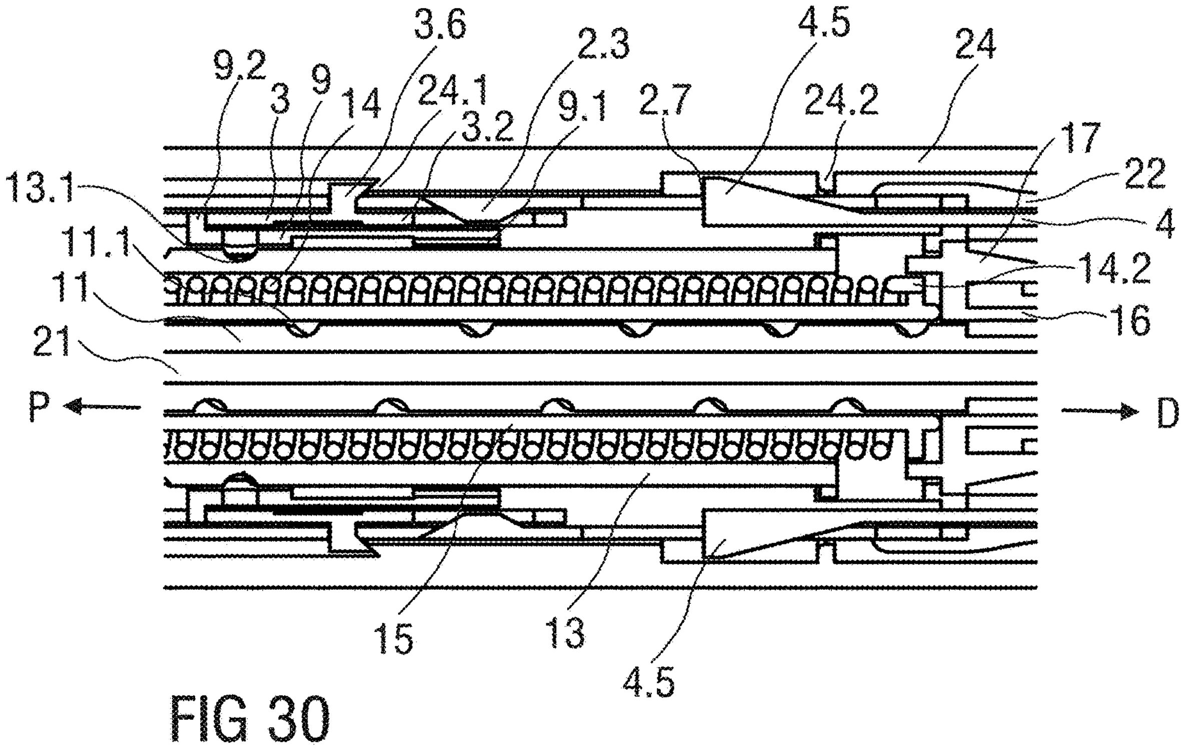
FIG. 30 is a detail view of an interlock mechanism between the sleeve trigger, the needle shroud and the end trigger button during an attempt to translate the sleeve trigger in proximal direction without prior depression of the needle shroud.
Figure 31:
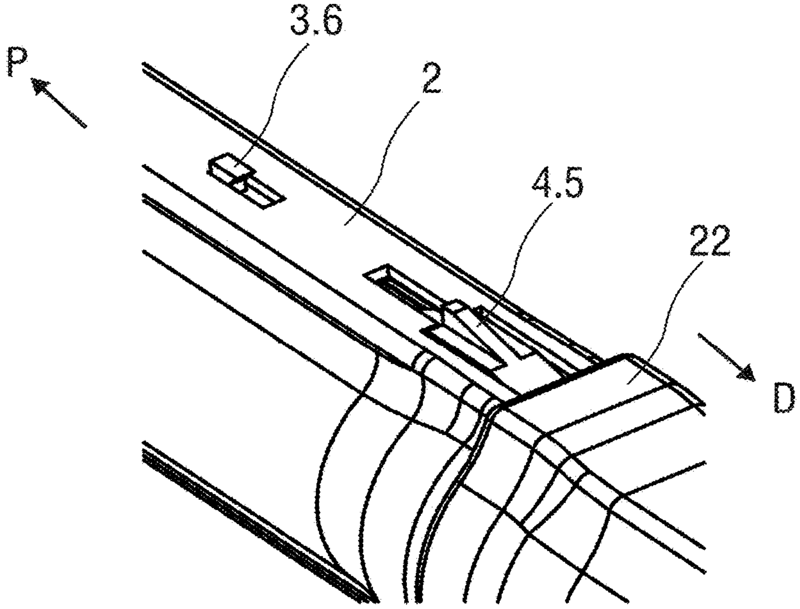
FIG. 31 is a detail view of locking features of the interlock mechanism.
Figure 32:
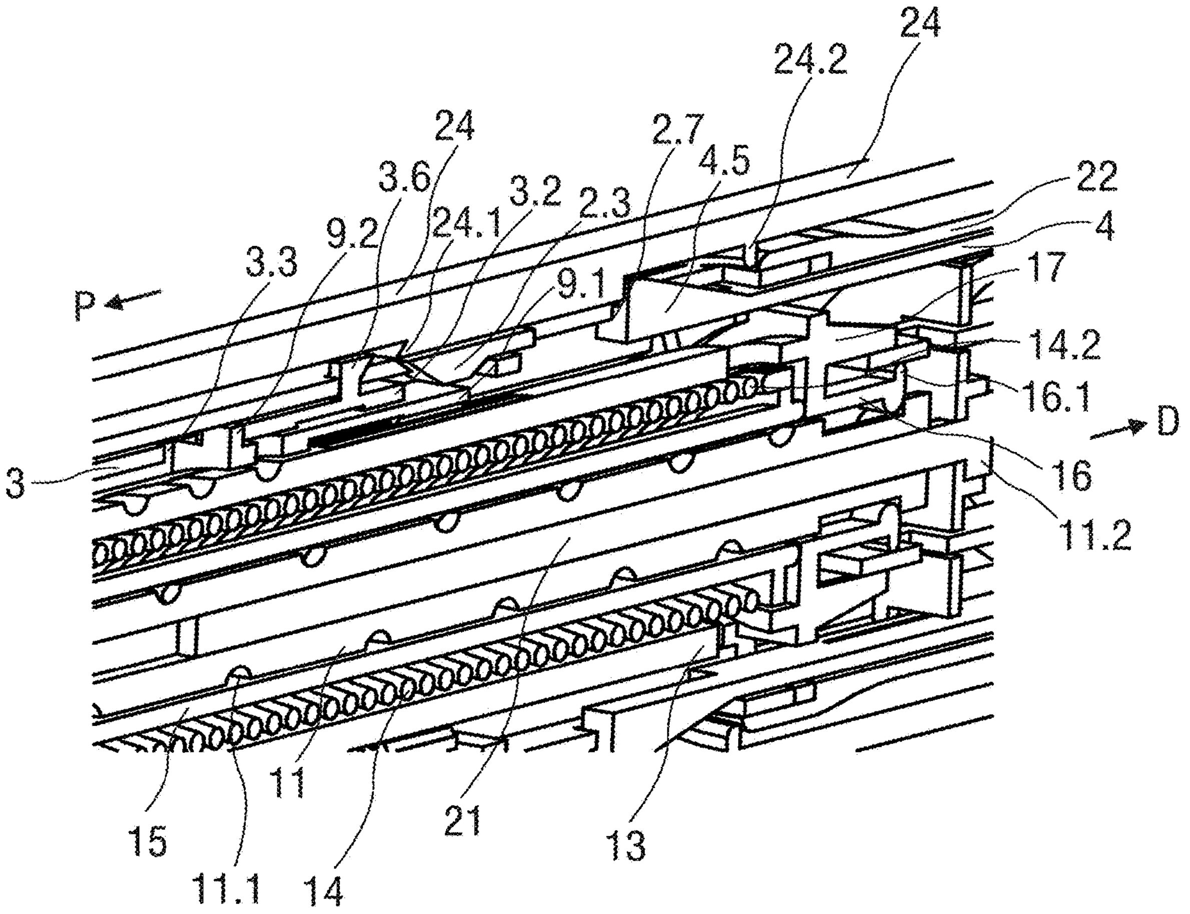
FIG. 32 is a sectional detail view of the locking features of the interlock mechanism.

FIG. 29 shows another alternative embodiment of the auto-injector 1 with a wrap over sleeve trigger 24 (e.g., an activating member) arranged over the distal end D and extending over roughly half the length of the housing 2. However, the auto-injector 1 also comprises the end trigger button 4 of the embodiment illustrated in FIGS. 1 to 24, but hidden inside the distal end D. A trigger spring 23 applies a load between the sleeve trigger 24 and the end trigger button 4. The load from the trigger spring 23 is balanced by load from the shroud spring 12. The end trigger button 4 exhibits latch features 4.5 initially abutted against a stop 2.7 in the housing 2 (see FIGS. 29 to 32).

The sequence of operation is as described above for the embodiment in FIGS. 1 to 24 except in the following steps:

The initial position and function of all components is identical with the exception of the button interlock. Movement of the trigger sleeve 24 is prevented to avoid unintended activation of the auto-injector 1. If the trigger sleeve 24 is moved, a locking feature 24.1 engages with a mating part 3.6 on the needle shroud 3 guarding against the user grabbing the housing 2 and attempting to operate the trigger sleeve 24 (see FIG. 30). When the auto-injector 1 is pressed against the skin, the needle shroud 3 translates within the housing 2 and the mating part 3.6 on the shroud 3 is inwardly withdrawn as the resilient third beam element 3.2 runs down a cam on the second rib 2.3 in the housing 2 allowing it to be depressed.

When ready to do so, the user translates the sleeve trigger 24 in proximal direction P. As the trigger sleeve 24 translates, a latch actuation boss 24.2 on the sleeve trigger 24 deflects the latch feature 4.5 inwards disengaging it from the stop 2.7 in the housing 2. The end trigger button 4 is then translated under the action of the trigger spring 23. This releases the chassis clip 16 resolving the axial load on the plunger 11.

This allows for a forced activation sequence. The intended activation of the auto-injector 1 involves the needle shroud 3 (skin interlock) being depressed prior to the trigger sleeve 24 being translated. Both parts (needle shroud 3 and trigger sleeve 24) are sprung relative to the housing 2 in this embodiment. By careful selection of the spring properties of the shroud spring 12 and the trigger spring 23, the correct sequence can be achieved. If the shroud spring 12 is less stiff than the trigger spring 23, it will compress first when a load is applied between the needle shroud 3 and the trigger sleeve 24. In the case of an end trigger button 4 only as in FIGS. 1 to 24, this is not required as the user holds the housing 2 and is able to move the two parts independently.

The embodiment of FIGS. 29 to 32 furthermore allows for a non-return activation sequence, i.e. the embodiment allows the needle shroud 3 to be depressed and the trigger sleeve 24 to be moved up to the point of release of the end trigger button 4 and then released without changing the load paths within the auto-injector 1. I.e. the auto-injector 1 can be placed on the skin and then removed and remain in a safe state. Once the trigger sleeve 24 moves beyond the point of release of the internal end trigger button 4, the auto-injector 1 is activated under the action of the trigger spring 23 and cannot be stopped by the user. This prevents the user partially activating the auto-injector 1 and leaving it in a partially activated state, which would result in the auto-injector firing immediately on the next attempt without requiring the sequenced operation.

Furthermore the embodiment demonstrates the ability to convert the auto-injector 1 from an end trigger (FIGS. 1 to 24) to a sleeve trigger (FIGS. 29 to 32) by adding an additional part, thus achieving a platform design.

The auto-injector 1 may preferably be used for delivering one of an analgetic, an anticoagulant, insulin, an insulin derivate, heparin, Lovenox, a vaccine, a growth hormone, a peptide hormone, a protein, antibodies and complex carbohydrates.

LIST OF REFERENCES

1 auto-injector
2 housing
2.1 first rib
2.2 first beam element
2.3 second rib
2.4 stop
2.5 snap
2.6 third rib
2.7 stop
2.8 step
3 needle shroud
3.1 second beam element
3.2 third beam element
3.3 slot hole
3.4 distal extension
3.5 window
3.6 mating part
4 trigger button, end trigger button, activating means
4.1 trigger beam
4.2 aperture
4.3 inward boss
4.4 snap
4.5 latch feature
5 spline
7 syringe
8 syringe carrier
8.1 rear flange
9 shroud follower, second gear member
9.1 fourth beam element
9.2 pin
10 stopper
11 plunger, second gear member
11.1 plunger lead screw thread
11.2 shoulder
12 shroud spring
13 shroud lead screw, first gear member
13.1 shroud lead screw thread
13.2 spline
13.3 circumferential outward boss
13.4 lip
13.5 flange
14 torsion spring, spring means
14.1 proximal end, first end
14.2 distal end, second end
15 plunger follower, first gear member
16 chassis clip
16.1 outward pin
17 support beam
18 protective needle shield
19 injection needle
20 lateral trigger button, activating means
20.1 boss
21 torque reaction rod
22 distal end cap
23 trigger spring
24 sleeve trigger, activating means
24.1 locking feature
24.2 latch actuation boss
D distal end, distal direction
M medicament
P proximal end, proximal direction

The invention claimed is:

1. An auto-injector comprising:

a housing comprising at least one viewing window, wherein at least a portion of the housing is cylindrical;

a syringe carrier disposed in the housing, the syringe carrier configured to hold a syringe within the housing, the syringe containing a medicament and having a needle configured to dispense the medicament;

a cap removably attached to a proximal end of the housing such that removal of the cap from the housing removes a protective needle shield from the needle while the syringe remains stationary within the housing when the syringe is disposed in the auto-injector;

a sleeve configured to move relative to the housing from a first position to a second position by a direct touch of a user;

a trigger button located at a distal end of the housing, the auto-injector configured such that (i) a proximal movement of the trigger button relative to the housing is limited when the sleeve is in the first position, and (ii) the proximal movement of the trigger button is allowed when the sleeve is in the second position, the trigger button comprising a proximally-extending portion;

a plunger having a proximal end configured to engage a stopper within the syringe, the auto-injector being configured such that two distally-extending resilient clips releasably hold the plunger in a distal position within the housing until the proximal movement of the trigger button relative to the housing allows the two distally-extending resilient clips to flex radially within the housing to release the plunger from being held in the distal position such that the plunger advances proximally within the housing to insert the needle of the syringe into an injection site and then to dispense the medicament from the syringe, wherein the plunger comprises a non-cylindrical portion configured to prevent a rotation of the plunger about a longitudinal axis of the housing during all proximal movement of the plunger within the housing, wherein the non-cylindrical portion is located along an axial portion of the plunger and prevents the rotation of the plunger throughout operation of the auto-injector;

a first member configured to rotate relative to the housing along the longitudinal axis of the housing after at least a portion of the medicament has been dispensed from the syringe;

a second member circumferentially surrounding the plunger and having a distal end that is distal to a distal end of the first member; and a torsion spring having a distal end engaged to the second member and a proximal end engaged to the first member, the torsion spring configured to apply a biasing force between the first member and the second member to rotate the first member relative to the second member after at least the portion of the medicament has been dispensed from the syringe, wherein the auto-injector is configured to produce an audible indication when the medicament has been dispensed from the syringe to indicate that an injection is substantially complete, and the auto-injector is configured to dispense the medicament from the syringe within 10 seconds.

2. The auto-injector of claim 1, wherein the non-cylindrical portion of the plunger has a rectangular shape defined by one or more axially-extending planar surfaces.

3. The auto-injector of claim 1, wherein the non-cylindrical portion of the plunger is configured to slidably engage an axial guide during the proximal movement of the plunger within the housing.

4. The auto-injector of claim 1, wherein the non-cylindrical portion of the plunger located along the axial portion of the plunger extends along a portion of an axial length of the plunger, the portion of the axial length being less than an entire axial length of the plunger.

5. The auto-injector of claim 1, wherein the sleeve moves axially between the first position and the second position.

6. The auto-injector of claim 1, wherein the two distally-extending resilient clips flex radially outward to release the plunger from being held in the distal position.

7. The auto-injector of claim 1, comprising the syringe, wherein the medicament in the syringe is a GLP-1 class drug.

8. An auto-injector comprising:

a housing comprising at least one viewing window, wherein at least a portion of the housing is cylindrical;

a syringe carrier disposed in the housing, the syringe carrier configured to hold a syringe within the housing, the syringe containing a medicament and having a needle configured to dispense the medicament;

a sleeve configured to move relative to the housing from a first position to a second position;

a button located at a distal end of the auto-injector, the auto-injector configured such that (i) a proximal movement of the button relative to the housing is limited when the sleeve is in the first position, and (ii) the proximal movement of the button is allowed when the sleeve is in the second position, the button comprising a proximally-extending portion;

a plunger having a proximal end configured to engage a stopper within the syringe and a distal end configured to hold the plunger in a distal position within the housing, the auto-injector configured such that two distally-extending resilient clips releasably hold the plunger in the distal position within the housing until the proximal movement of the button relative to the housing allows the two distally-extending resilient clips to flex radially to release the plunger from being held in the distal position such that the plunger advances proximally within the housing for needle insertion and to dispense the medicament from the syringe, wherein the plunger comprises a non-cylindrical portion that extends along a portion of an axial length of the plunger, the portion of the axial length being less than an entire axial length of the plunger, wherein the non-cylindrical portion is configured to prevent a rotation of the plunger about a longitudinal axis of the housing during all proximal movement of the plunger within the housing, and wherein the non-cylindrical portion prevents the rotation of the plunger throughout operation of the auto-injector;

a first member configured to rotate relative to the housing along a longitudinal axis of the housing after at least a portion of the medicament has been dispensed from the syringe;

a second member surrounding the plunger, the second member having an axial length that is greater than an axial length of the first member, and a torsion spring configured to apply a biasing force between the first member and the second member to rotate the first member relative to the second member after at least the portion of the medicament has been dispensed from the syringe, wherein the auto-injector is configured to produce an audible indication when the medicament has been dispensed from the syringe to indicate that an injection is substantially complete.

9. The auto-injector of claim 8, wherein the auto-injector is configured to dispense the medicament from the syringe within approximately 10 seconds.

10. The auto-injector of claim 8, wherein the auto-injector is configured to allow a user to hold the auto-injector against an injection site for approximately 10 seconds to inject the medicament into the injection site.

11. The auto-injector of claim 8, wherein the auto-injector is configured such that a proximal end of the first member is proximal to a proximal end of the second member, and a distal end of the second member is distal to a distal end of the first member.

12. The auto-injector of claim 8, wherein the auto-injector is configured such that a distal end of the torsion spring is engaged to the second member, and a proximal end of the torsion spring is engaged to the first member.

13. The auto-injector of claim 8, wherein the two distally-extending resilient clips are disposed diametrically opposite of one another, and the auto-injector is configured such that a ramped engagement involving the plunger allows the plunger to be released from being held in the distal position.

14. The auto-injector of claim 8, comprising a cap removably attached to a proximal end of the housing such that removal of the cap from the housing removes a protective needle shield from the needle while the syringe remains stationary within the housing.

15. The auto-injector of claim 8, comprising the syringe, wherein the medicament in the syringe is a GLP-1 class drug.

* * * * *